US012385018B2

(12) United States Patent
Arikawa et al.

(10) Patent No.: US 12,385,018 B2
(45) Date of Patent: Aug. 12, 2025

(54) TRANSFORMED MICROORGANISM AND METHOD OF PRODUCING POLYHYDROXYALKANOATE

(71) Applicant: KANEKA CORPORATION, Osaka (JP)

(72) Inventors: Hisashi Arikawa, Takasago (JP); Shunsuke Sato, Takasago (JP)

(73) Assignee: KANEKA CORPORATION, Osaka (JP)

( * ) Notice: Subject to any disclaimer, the term of this patent is extended or adjusted under 35 U.S.C. 154(b) by 881 days.

(21) Appl. No.: 17/412,340

(22) Filed: Aug. 26, 2021

(65) Prior Publication Data
US 2021/0388324 A1    Dec. 16, 2021

Related U.S. Application Data

(63) Continuation of application No. PCT/JP2020/003156, filed on Jan. 29, 2020.

(30) Foreign Application Priority Data

Feb. 28, 2019  (JP) ................................ 2019-036006
Feb. 28, 2019  (JP) ................................ 2019-036008

(51) Int. Cl.
*C12N 9/10*       (2006.01)
*C12P 7/625*      (2022.01)

(52) U.S. Cl.
CPC ............ *C12N 9/1029* (2013.01); *C12P 7/625* (2013.01)

(58) Field of Classification Search
None
See application file for complete search history.

(56) References Cited

U.S. PATENT DOCUMENTS

| | | | | |
|---|---|---|---|---|
| 9,175,317 | B2 * | 11/2015 | Sato | ........................ C12N 15/74 |
| 10,072,255 | B2 * | 9/2018 | Arikawa | ........ C12Y 402/01074 |
| 11,453,896 | B2 * | 9/2022 | Arikawa | ........ C12Y 203/01009 |
| 2019/0153486 | A1 | 5/2019 | Arikawa et al. | |
| 2020/0087687 | A1 | 3/2020 | Aoki et al. | |

FOREIGN PATENT DOCUMENTS

| | | |
|---|---|---|
| CN | 104762311 A | 7/2015 |
| CN | 105779488 A | 7/2016 |
| EP | 4 029 946 A1 | 7/2022 |
| WO | WO 2018/021046 A1 | 2/2018 |
| WO | WO 2018/216726 A1 | 11/2018 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession G0ES24. Oct. 19, 2011 (Year: 2011).*
Accession A0A022FNJ8. Jun. 11, 2014. (Year: 2014).*
Accession A0A212MH45. Sep. 27, 2017 (Year: 2017).*
Accession A0A022FQN4. Jun. 11, 2014 (Year: 2014).*
Tan et al., "Engineering *Halomonas* TD01 for the low-cost production of polyhydroxyalkanoates", Metabolic Engineering, 2014, vol. 26, pp. 34-47.
Uniprot, [online], Accession No. Q0KFI4, URL<https://www.uniprot.org/uniprotkb/Q0KFI4/entry >, as cited in the Office Action issued on Jan. 30, 2024 in Japanese counterpart Application No. 2021-501778. 4 pages.
NCBI Database, [online], Accession No. WP_010811452.1, URL<https://www.ncbi.nlm.nih.gov/protein/498510994?sat=47&satkey=62716682 >, as cited in the Office Action issued on Jan. 30, 2024 in Japanese counterpart Application No. 2021-501778, 1 page.
UniProt, [online], Accession No. Q0KFI3, URL<https://www.uniprot.org/uniprotkb/Q0KFI3/entry >, as cited in the Office Action issued on Jan. 30, 2024 in Japanese counterpart Application No. 2021-501778, 4 pages.
NCBI Database, [online], Accession No. WP_010811453.1, URL<https://www.ncbi.nlm.nih.gov/protein/498510995?sat=47&satkey=68081467 >, as cited in the Office Action issued on Jan. 30, 2024 in Japanese counterpart Application No. 2021-501778, 1 page.
UniProt, [online], Accession No. Q0KFI5, URL<https://www.uniprot.org/uniprotkb/Q0KFI5/entry >, as cited in the Office Action issued on Jan. 30, 2024 in Japanese counterpart Application No. 2021-501778, 4 pages.
NCBI Database, [online], Accession No. WP_010811451.1, URL<https://www.ncbi.nlm.nih.gov/protein/498510993?sat=47&satkey=42867008 >, as cited in the Office Action issued on Jan. 30, 2024 in Japanese counterpart Application No. 2021-501778, 1 page.
International Search Report dated Apr. 14, 2020, in PCT/JP2020/003156, filed Jan. 29, 2020.
Anderson A.J. et al., *Int. J. Biol. Macromol.*, 12, 102-105 (1990).
Sato S. et al., *J. Biosci. Bioeng.*, 120(3), 246-251 (2015).
Insomphun C. et al., *Metab.Eng.*, 27, 38-45 (2015).
Pichoff, s. et al., "Deletion analysis of gene minE which encodes the topological specificity factor of cell division in *Escherichia coil*", Molecular Microbiology, 1995, vol. 18, No. 2, pp. 321-329.
Sato, Shunsuke et al., "Process development of biodegradable polymer PHBH", Seibutsu-kogaku kaishi, Feb. 25, 2019, vol. 97, No. 2, pp. 66-74.

* cited by examiner

*Primary Examiner* — Christian L Fronda
(74) *Attorney, Agent, or Firm* — Oblon, McClelland, Maier & Neustadt, L.L.P.

(57) ABSTRACT

Provided is a transformed microorganism that has a polyhydroxyalkanoate synthase gene and in which expression of a minD gene is enhanced. Also provided is a transformed microorganism that has a polyhydroxyalkanoate synthase gene and in which expression of a minC gene and a minD gene is enhanced. In this transformed microorganism, expression of a minE gene may be enhanced or reduced. Also provided is a method of producing a PHA, the method including the step of culturing any of the transformed microorganisms in the presence of a carbon source.

20 Claims, 4 Drawing Sheets

Specification includes a Sequence Listing.

Comp. Example 1

Comp. Example 2

Comp. Example 3

Comp. Example 4

Example 1

Example 2

Example 3

Example 4

TRANSFORMED MICROORGANISM AND METHOD OF PRODUCING POLYHYDROXYALKANOATE

CROSS REFERENCE TO RELATED APPLICATIONS

This application is a continuation of International Application No. PCT/JP2020/003156, filed Jan. 29, 2020, and claims priority to Japanese Application No. 2019-036006, filed Feb. 28, 2019, and Japanese Application No. 2019-036008, filed Feb. 28, 2019, the disclosures of all of which are incorporated herein by reference in their entireties.

TECHNICAL FIELD

The present invention relates to a transformed microorganism capable of elaborating a polyhydroxyalkanoate and a method of producing the polyhydroxyalkanoate using the transformed microorganism.

BACKGROUND ART

There is a growing awareness of environmental issues, food issues, health, and safety, and more and more people are becoming nature-oriented. Against such a background, material production using microorganisms (such as fermentative production and bioconversion) is becoming increasingly significant and important. Microbial material production is applied also to production of protein pharmaceuticals and production of nucleic acids for gene therapy. For example, ethanol production, acetic acid production, and medical protein production using microorganisms such as yeasts and bacteria are actively employed industrially.

An example of the microbial material production is microbial production of polyhydroxyalkanoates (occasionally referred to as "PHAs" hereinafter) which are considered promising biodegradable plastics for industrial use (see Non Patent Literature 1). PHAs are thermoplastic polyesters produced and accumulated as energy storage materials in cells of many kinds of microorganisms and are biodegradable. Nowadays, the heightened environmental awareness has led to increasing attention to non-petroleum-based plastics. In particular, there is a strong demand for practical use of PHAs produced and accumulated in microorganisms because such PHAs are absorbed into the carbon circulation process in the nature and are therefore expected to have little adverse impact on the ecosystems. A known example of PHA production using microorganisms is to produce a PHA by feeding bacteria of the genus *Cupriavidus* with a carbon source such as a sugar, vegetable oil, or fatty acid and thus allowing the bacteria to accumulate the PHA in their cells (see Non Patent Literatures 2 and 3).

However, microbial material production requires the complicated steps of separating and collecting the microbial cells and the target product and could suffer the problem of high production cost. Improving the efficiency of separation and collection is a major challenge to be addressed for production cost reduction.

CITATION LIST

Non-Patent Literature

NPL 1: Anderson A. J. et al., *Int. J. Biol. Macromol.*, 12, 102-105 (1990)

NPL 2: Sato S. et al., *J. Biosci. Bioeng.*, 120 (3), 246-251 (2015)

NPL 3: Insomphun C. et al., *Metab. Eng.*, 27, 38-45 (2015)

SUMMARY OF INVENTION

Technical Problem

A PHA is accumulated in microbial cells. To use the PHA accumulated in the microbial cells as a biodegradable plastic, it is necessary first to separate and collect the microbial cells from the culture fluid. The separation and collection of the microbial cells can be conducted by means such as a centrifuge or separation membrane, and the ease and efficiency of the separation and collection depend on the size of the microbial cells. Specifically, a larger size of the microbial cells allows the separation and collection to be more easily and efficiently accomplished by means such as a centrifuge or separation membrane, leading to a lower production cost.

The microbial cells accumulating the PHA are broken to take PHA particles out of the cells, and the PHA particles are separated from other cellular components and collected. Techniques for the separation and collection of the PHA particles are broadly classified into a technique using an organic solvent system and a technique using an aqueous system. Since the use of an organic solvent causes high environmental load and involves high cost, the technique using an aqueous system is preferred from the industrial point of view. With the technique using an aqueous system, for example, the PHA particles contained in the broken cell fluid can be separated from the fluid by means such as a centrifuge or separation membrane. In this case, the efficiency of the separation and collection depends on the size of the PHA particles. Specifically, a larger size of the PHA particles accumulated in the microbial cells allows the separation and collection to be more easily accomplished by means such as a centrifuge or separation membrane, leading to a lower production cost.

In view of the above circumstances, the present invention aims to provide a transformed microorganism that accumulates a PHA and whose size can be large and a method of producing the PHA using the transformed microorganism.

Solution to Problem

As a result of intensive studies, the present inventors have found that when the expression of a particular one of genes expected to be involved in cell division, namely, a minC gene (e.g., a gene that encodes the amino acid sequence of SEQ ID NO: 1), a minD gene (e.g., a gene that encodes the amino acid sequence of SEQ ID NO: 2), and a minE gene (e.g., a gene that encodes the amino acid sequence of SEQ ID NO: 3), is enhanced or reduced, the size of microbial cells can be increased while ensuring an industrially desired level of PHA accumulation. Based on this finding, the inventors have arrived at the present invention.

That is, the present invention relates to a transformed microorganism having a polyhydroxyalkanoate synthase gene, wherein expression of a minD gene is enhanced. The present invention further relates to a transformed microorganism having a polyhydroxyalkanoate synthase gene, wherein expression of a minC gene and a minD gene is enhanced. In this transformed microorganism, expression of a minE gene may be enhanced or reduced. The above transformed microorganisms preferably belong to the genus *Cupriavidus* and are more preferably transformed *Cupria-*

*vidus necator*. The present invention further relates to a method of producing a polyhydroxyalkanoate, the method including the step of culturing any of the transformed microorganisms in the presence of a carbon source. The carbon source preferably contains an oil, a fatty acid, a sugar, or carbon dioxide. The polyhydroxyalkanoate is preferably a copolymer of two or more hydroxyalkanoates, more preferably a copolymer containing 3-hydroxyhexanoate as a monomer unit, and even more preferably a copolymer of 3-hydroxybutyrate and 3-hydroxyhexanoate.

Advantageous Effects of Invention

The present invention can provide a transformed microorganism that accumulates a PHA and whose size can be large and a method of producing the PHA using the transformed microorganism. In the present invention, since the size of microbial cells accumulating the PHA is large, the microbial cells can easily be separated and collected from a culture fluid, and the production cost can be reduced.

A preferred aspect of the present invention can provide a transformed microorganism whose size can be large and that is capable of accumulating large-size PHA particles and a method of producing a PHA using the transformed microorganism. In this aspect, not only are the separation and collection of microbial cells from a culture fluid easy, but also large-size PHA particles are accumulated in the microbial cells. Thus, the PHA can easily be collected separately from other cellular components after cell breakage, and the production cost can be reduced.

DESCRIPTION OF EMBODIMENTS

Figure 1:
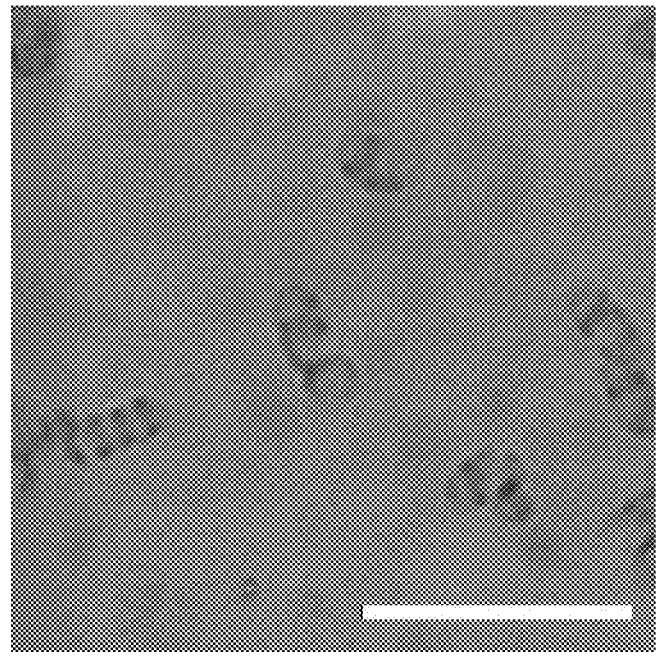
FIG. 1 is a microscope image of a cultured KNK-005 strain (Comparative Example 1), where the scale bar represents 10 μm (the same applies to FIGS. 2 to 8).

Hereinafter, embodiments of the present invention will be described in detail. A transformed microorganism according to the present invention is a transformed microorganism that has a PHA synthase gene and in which expression of a particular one of minC, minD, and minE genes is enhanced or reduced.

Microorganism

The transformed microorganism according to the present invention may be a microorganism having a PHA synthase gene and transformed to enhance the expression of the minD gene. Alternatively, the transformed microorganism may be a microorganism having a PHA synthase gene and transformed to enhance the expression of the minC and minD genes. Alternatively, the transformed microorganism may be a microorganism having a PHA synthase gene and transformed to enhance the expression of the minC, minD, and minE genes or may be a microorganism having a PHA synthase gene and transformed to enhance the expression of the minC and minD genes and reduce the expression of the minE gene. It should be noted that a microorganism transformed to enhance the expression of the minD gene and reduce the expression of the minE gene and not having enhanced expression of the minC gene is not categorized as the transformed microorganism of the present invention.

The host of the transformed microorganism according to the present invention is not limited to a particular type, and may be any microorganism that has a PHA synthase gene. The host is preferably a bacterium having a minCD or minCDE gene. Examples of the bacterium include bacteria belonging to the genus *Ralstonia*, the genus *Cupriavidus*, the genus *Wautersia*, the genus *Aeromonas*, the genus *Escherichia*, the genus *Alcaligenes*, and the genus *Pseudomonas*. In view of safety and PHA productivity, bacteria belonging to the genus *Ralstonia*, the genus *Cupriavidus*, the genus *Aeromonas*, and the genus *Wautersia* are more preferred. Even more preferred are bacteria belonging to the genus *Cupriavidus* or the genus *Aeromonas*, and still even more preferred are microorganisms belonging to the genus *Cupriavidus*. Particularly preferred is *Cupriavidus necator*.

The host of the transformed microorganism according to the present invention may be a wild strain inherently having a PHA synthase gene, a mutant strain obtained by artificially mutating the wild strain, or a strain having a foreign PHA synthase gene introduced by a genetic engineering technique. The introduction of the foreign PHA synthase gene is not limited to being carried out by a particular method, and the introduction method can be selected from: a method in which the foreign gene is directly inserted onto the chromosome of the host or a gene on the chromosome is replaced by the foreign gene; a method in which the foreign gene is directly inserted onto the megaplasmid of the host or a gene on the megaplasmid is replaced by the foreign gene; and a method in which the foreign gene is placed on a vector such as a plasmid, phage, or phagemid and the vector with the gene is introduced into the host. Two or more of these methods may be used in combination. In view of the stability of the introduced gene, it is preferable to use the method in which the foreign gene is directly inserted onto the chromosome of the host or a gene on the chromosome is replaced by the foreign gene or the method in which the foreign gene is directly inserted onto the megaplasmid of the host or a gene on the megaplasmid is replaced by the foreign gene, and it is more preferable to use the method in which the foreign gene is directly inserted onto the chromosome of the host or a gene on the chromosome is replaced by the foreign gene.

PHA Synthase Gene

The PHA synthase gene is not limited to a particular type, and examples of the PHA synthase gene include PHA synthase genes derived from living organisms belonging to the genus *Ralstonia*, the genus *Cupriavidus*, the genus *Wautersia*, the genus *Alcaligenes*, the genus *Aeromonas*, the genus *Pseudomonas*, the genus *Norcardia*, and the genus *Chromobacterium*, and further include altered genes resulting from alteration of the mentioned PHA synthase genes.

Such an altered gene may be a gene having a base sequence that encodes a PHA synthase in which one or more amino acid residues are deleted, added, inserted, or replaced. Examples of the altered gene include a gene having a base sequence that encodes a polypeptide represented by an amino acid sequence of any one of SEQ ID NOS: 4 to 8 and a gene having a base sequence that encodes a polypeptide having PHA synthase activity and represented by an amino acid sequence that is at least 85% homologous to the amino acid sequence of any one of SEQ ID NOS: 4 to 8. The sequence homology is preferably 90% or more, more preferably 95% or more, even more preferably 97% or more, and particularly preferably 99% or more.

PHA

The PHA produced by the transformed microorganism of the present invention is not limited to a particular type, and may be any PHA that can be produced by microorganisms. The PHA is preferably any one of the following polymers: a homopolymer of one monomer selected from 3-hydroxyalkanoates having 4 to 16 carbon atoms; a copolymer of one monomer selected from 3-hydroxyalkanoates having 4 to 16 carbon atoms and another hydroxyalkanoic acid (such as a 2-hydroxyalkanoic acid, 4-hydroxyalkanoic acid, 5-hydroxyalkanoic acid, or 6-hydroxyalkanoic acid having 4 to 16 carbon atoms); and a copolymer of two or more monomers selected from 3-hydroxyalkanoates having 4 to 16 carbon atoms. Examples of the PHA include, but are not limited to: P(3HB) which is a homopolymer of 3-hydroxybutyrate (abbreviated as 3HB); P(3HB-co-3HV) which is a copolymer of 3HB and 3-hydroxyvaleric acid (abbreviated as 3HV); P(3HB-co-3HH) (abbreviated as PHBH) which is a copolymer of 3HB and 3-hydroxyhexanoate (abbreviated as 3HH); P(3HB-co-4HB) which is a copolymer of 3HB and 4-hydroxybutyrate (abbreviated as 4HB); and PHA containing lactic acid (abbreviated as LA) as a constituent component (an example of this PHA is P(LA-co-3HB) which is a copolymer of 3HB and LA). Among these examples, PHBH is preferred in that this polymer has a wide range of applications. The type of the PHA to be produced can be appropriately selected according to the intended purpose and depending on the type of the PHA synthase gene possessed by or introduced into the microorganism used, the type of the metabolizing gene involved in synthesis of the PHA, and the culture conditions.

minC, minD, and minE Genes

Proteins MinC, MinD, and MinE encoded by the minC, minD, and minE genes are proteins that cooperate in bacteria to control cell division (MinCDE system). For example, it is known that in cells of *Escherichia coli*, the MinD forms a polymer in an ATP-dependent manner, further forms a complex with the MinC, and rapidly oscillates between the cell poles. The MinC serves to inhibit septum formation during cell division. The MinE is known to bind to the MinD competitively against the MinC, and serves to regulate septum formation so that the septum is formed only at the center of the cell.

The minC gene is a gene having a base sequence that encodes a polypeptide (UniProtKB ID Q0KFI3) represented by the amino acid sequence of SEQ ID NO: 1 and a polypeptide represented by an amino acid sequence that is at least 85% homologous to the amino acid sequence of SEQ ID NO: 1. The sequence homology is preferably 90% or more, more preferably 95% or more, even more preferably 97% or more, and particularly preferably 99% or more.

The minD gene is a gene having a base sequence that encodes a polypeptide (UniProtKB ID Q0KFI4) represented by the amino acid sequence of SEQ ID NO: 2 and a polypeptide represented by an amino acid sequence that is at least 85% homologous to the amino acid sequence of SEQ ID NO: 2. The sequence homology is preferably 90% or more, more preferably 95% or more, even more preferably 97% or more, and particularly preferably 99% or more.

The minE gene is a gene having a base sequence that encodes a polypeptide (UniProtKB ID Q0KFI5) represented by the amino acid sequence of SEQ ID NO: 3 and a polypeptide represented by an amino acid sequence that is at least 85% homologous to the amino acid sequence of SEQ ID NO: 3. The sequence homology is preferably 90% or more, more preferably 95% or more, even more preferably 97% or more, and particularly preferably 99% or more.

Gene Expression Enhancement

In the present invention, enhanced gene expression means a state in which the amount of transcription of a target gene or the amount of expression of the polypeptide encoded by the target gene is increased as compared to that in a strain in which the expression of the target gene is not enhanced. The increase is not limited to a particular level, and it is sufficient that the amount of transcription of the target gene or the amount of expression of the polypeptide be more than that in the strain in which the expression of the target gene is not enhanced. The amount of transcription of the target gene or the amount of expression of the polypeptide is preferably 1.1 or more times, more preferably 1.2 or more times, even more preferably 1.5 or more times, and still even more preferably 2 or more times that in the strain in which the expression of the target gene is not enhanced.

In the present invention, the enhancement of the expression of the min genes is not limited to being carried out by a particular method, and the enhancement method can be selected from a method in which the target gene is introduced into the host and a method in which the amount of expression of the target gene inherently possessed by the host on the genome DNA is increased. Both of the two methods may be used in combination.

The introduction of the target gene into the host is not limited to being carried out by a particular method, and the introduction method can be selected from: a method in which the target gene is directly inserted onto the chromosome of the host or a gene on the chromosome is replaced by the target gene; a method in which the target gene is directly inserted onto the megaplasmid of the host or a gene on the megaplasmid is replaced by the target gene; and a method in which the target gene is placed on a vector such as a plasmid, phage, or phagemid and the vector with the gene is introduced into the host. Two or more of these methods may be used in combination.

In view of the stability of the introduced gene, it is preferable to use the method in which the target gene is directly inserted onto the chromosome of the host or a gene on the chromosome is replaced by the target gene or the method in which the target gene is directly inserted onto the megaplasmid of the host or a gene on the megaplasmid is replaced by the target gene, and it is more preferable to use the method in which the target gene is directly inserted onto the chromosome of the host or a gene on the chromosome is replaced by the target gene. For reliable expression of the introduced gene, it is preferable to introduce the target gene in such a manner that the target gene is downstream of a "gene expression regulatory sequence" inherently possessed by the host or downstream of a foreign "gene expression regulatory sequence". In the present invention, a "gene expression regulatory sequence" is a DNA sequence including a base sequence that controls the amount of transcription of the gene (an example of this base sequence is a promotor sequence) and/or a base sequence that regulates the amount of translation of a messenger RNA transcribed from the gene (an example of this base sequence is a Shine-Dalgarno sequence). The "gene expression regulatory sequence" used may be any suitable naturally-occurring base sequence or an artificially constructed or altered base sequence.

The increase of the amount of expression of the target gene inherently possessed by the host on the genome DNA is not limited to being achieved by a particular method, and exemplary methods include a method in which a "gene expression regulatory sequence" upstream of the target gene is altered, a method in which a foreign "gene expression regulatory sequence" is introduced upstream of the target gene, and a method in which the target gene and/or a base sequence neighboring the target gene is altered to increase the stability of the transcribed messenger RNA.

Examples of the promotor sequence or Shine-Dalgarno sequence included in the "gene expression regulatory sequence" include, but are not limited to, the base sequences of SEQ ID NOS: 9 to 15 and base sequences including any part of the base sequences of SEQ ID NOS: 9 to 15.

Replacement, deletion, insertion, and/or addition made to at least a part of the genome DNA can be accomplished using a method known to those skilled in the art. Typical methods include a method using a transposon and the mechanism of homologous recombination (Ohman et al., *J. Bacteriol.*, 162:1068-1074 (1985)) and a method based on site-specific integration caused by the mechanism of homologous recombination and on loss due to secondary homologous recombination (Noti et al., *Methods Enzymol.*, 154:197-217 (1987)). A method may also be used in which a sacB gene derived from *Bacillus subtilis* is allowed to coexist and in which a microorganism strain having lost a gene due to secondary homologous recombination is easily isolated as a sucrose-resistant strain (Schweizer, *Mol. Microbiol.*, 6:1195-1204 (1992) or Lenz et al., *J. Bacteriol.*, 176:4385-4393 (1994)). Another alternative method is to use a CRISPR/Cas9 system-based genome-editing technology for altering the target DNA (Y. Wang et al., *ACS Synth Biol.*, 2016, 5 (7):721-732). In the CRISPR/Cas9 system, the guide RNA (gRNA) has a sequence capable of binding to a part of the base sequence of the genome DNA to be altered, and serves to transport the Cas9 to the target.

The introduction of a vector into a cell is not limited to being carried out by a particular method, and exemplary methods include calcium chloride transformation, electroporation, polyethylene glycol transformation, and spheroplast transformation.

Gene Expression Reduction

In the present invention, "reduced gene expression" means a state in which the amount of transcription of a target gene or the amount of expression of the polypeptide encoded by the target gene is decreased as compared to that in a strain in which the expression of the target gene is not reduced. The decrease is not limited to a particular level, and it is sufficient that the amount of transcription of the target gene or the amount of expression of the polypeptide be less than that in the strain in which the expression of the target gene is not reduced. The amount of transcription of the target gene or the amount of expression of the polypeptide is preferably 0.8 or less times, more preferably 0.5 or less times, even more preferably 0.3 or less times, and still even more preferably 0.2 or less times that in the strain in which the expression of the target gene is not reduced. The amount of transcription of the target gene or the amount of expression of the polypeptide encoded by the target gene may be zero. The gene expression can be considered to have been reduced also when the polypeptide encoded by the target gene cannot exhibit the original function for a reason such as alteration of the base sequence of the gene. In the case where the transformed microorganism of the present invention is a transformed microorganism with enhanced expression of the minC and minD genes, the expression of the target gene can be reduced by using a drug or protein that inhibits the function of the corresponding polypeptide.

In the present invention, the reduction of the gene expression is not limited to being achieved by a particular method, and exemplary methods include: a method in which a part or the entire length of the target gene is deleted; a method in which the "gene expression regulatory sequence" involved in the expression of the target gene is altered; and a method in which the target gene and/or a base sequence neighboring the target gene is altered to decrease the stability of the transcribed messenger RNA. The base sequence alteration is not limited to being carried out by a particular method, and can be accomplished through replacement, deletion, insertion, and/or addition made to at least a part of the target gene and/or the neighboring base sequence. The replacement, deletion, insertion, and/or addition can be made by a method known to those skilled in the art. In the case where the transformed microorganism of the present invention is a transformed microorganism with enhanced expression of the minC and minD genes, an antisense RNA, RNA interference (RNAi), or CRISPR interference (CRISPRi) may be used to reduce the expression of the target gene without altering the target gene and/or the neighboring base sequence.

Culturing the transformed microorganism of the present invention allows the microorganism to accumulate a PHA therein. The culture of the transformed microorganism of the present invention can be conducted according to a common microbial culture method, and it is sufficient that the transformed microorganism be cultured in a culture medium containing a suitable carbon source. There are no particular limitations on the composition of the culture medium, the method of adding the carbon source, the scale of the culture, the conditions of aeration and stirring, the culture temperature, and the culture time. It is preferable to add the carbon source continuously or intermittently to the culture medium.

The carbon source used for the culture may be any carbon source that can be assimilated by the transformed microorganism of the present invention. Examples of the carbon source include, but are not limited to: sugars such as glucose, fructose, and sucrose; palm and palm kernel oils (including palm olein, palm double olein, and palm kernel olein which are low-melting fractions obtained through fractionation of palm oil and palm kernel oil); oils such as corn oil, coconut oil, olive oil, soybean oil, rapeseed oil, and Jatropha oil; fractions of these oils; by-products formed during refining of these oils; fatty acids such as lauric acid, oleic acid, stearic acid, palmitic acid, and myristic acid; derivatives of these fatty acids; and glycerol. In the case where the transformed microorganism of the present invention can assimilate gases such as carbon dioxide, carbon monoxide, and methane or alcohols such as methanol and ethanol, any of these gases or alcohols can be used as the carbon source.

In the PHA production of the present invention, it is preferable to culture the microorganism using a culture medium containing the carbon source and other nutrient sources including a nitrogen source, an inorganic salt, and another organic nutrient source. Examples of the nitrogen source include, but are not limited to: ammonia; ammonium salts such as ammonium chloride, ammonium sulfate, and ammonium phosphate; peptone; meat extracts; and yeast extracts. Examples of the inorganic salt include potassium dihydrogen phosphate, sodium dihydrogen phosphate, magnesium phosphate, magnesium sulfate, and sodium chloride. Examples of the other organic nutrient source include: amino acids such as glycine, alanine, serine, threonine, and proline; and vitamins such as vitamin B1, vitamin B12, and vitamin C.

After the microorganism is cultured for an adequate time to allow the microorganism to accumulate a PHA therein, the PHA is collected from the microorganism using a known method. The PHA collection is not limited to being carried out by a particular method. For example, the PHA can be collected by a method consisting of: after the culture, separating the microorganism from the culture fluid by means such as a centrifuge or separation membrane; drying the separated microorganism; extracting the PHA from the dried microorganism using an organic solvent such as chloroform; removing cellular components from the PHA-containing organic solvent solution by a process such as filtration; adding a poor solvent such as methanol or hexane to the filtrate to precipitate the PHA; removing the supernatant by a process such as filtration or centrifugation; and drying the precipitated PHA. Alternatively, the PHA may be collected by dissolving cellular components other than the PHA in water with the aid of a surfactant, an alkali, or an enzyme, then separating the PHA particles from the aqueous phase by a process such as filtration or centrifugation, and drying the separated PHA particles.

In the present invention, large-size microbial cells accumulating PHA can be obtained, and the microbial cells can be separated from the culture fluid easily and efficiently thanks to their large size. Large-size PHA particles producible according to a preferred aspect of the present invention are preferred because such PHA particles are easy to separate and collect using an aqueous system as described above.

EXAMPLES

Hereinafter, the present invention will be described more specifically using examples. The present invention is not limited to the examples. The overall genetic manipulation can be carried out, for example, in a manner as taught in Molecular Cloning (Cold Spring Harbor Laboratory Press (1989)). The enzymes and cloning hosts used in the gene manipulation can be purchased from market suppliers and used according to the instructions given by the suppliers. The enzymes are not limited to particular types and may be any enzymes that can be used for gene manipulation.

(Production Example 1) Preparation of minE Gene-Deleted Strain

First, a gene deletion plasmid was prepared. The preparation was done as follows. PCR using a synthetic oligo DNA was carried out to obtain a DNA fragment (SEQ ID NO: 16) having base sequences upstream and downstream of the minE structural gene. The DNA fragment was digested by a restriction enzyme SwaI, and the resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a gene deletion plasmid vector pNS2X-sacB+minEUD having base sequences upstream and downstream of the minE structural gene was prepared.

Subsequently, a minE gene-deleted strain was prepared using the gene deletion plasmid vector pNS2X-sacB+minEUD as follows. An *Escherichia coli* S17-1 strain (ATCC 47055) was transformed with the gene deletion plasmid vector pNS2X-sacB+minEUD, and the resulting transformed microorganism was cocultured with a KNK-005 strain on Nutrient Agar (manufactured by Difco Laboratories) to effect conjugal transfer. The KNK-005 strain is a transformed strain produced by introducing an *Aeromonas caviae*-derived PHA synthase gene (a gene that encodes a PHA synthase that has the amino acid sequence of SEQ ID NO: 6) onto the chromosome of a *Cupriavidus necator* H16 strain, and can be prepared according to the method described in U.S. Pat. No. 7,384,766.

The culture fluid obtained as above was inoculated into a Simmons agar medium (2 g/L sodium citrate, 5 g/L sodium chloride, 0.2 g/L magnesium sulfate heptahydrate, 1 g/L ammonium dihydrogen phosphate, 1 g/L potassium dihydrogen phosphate, 15 g/L agar, pH=6.8) containing 250 mg/L of kanamycin, and a strain grown on the agar medium was selectively collected. Thus, a strain having the plasmid integrated into the chromosome of the KNK-005 strain was obtained. The obtained strain was cultured on Nutrient Broth (manufactured by Difco Laboratories) for two generations, after which the culture broth was diluted and applied onto Nutrient Agar containing 15% sucrose. A strain grown on Nutrient Agar was obtained as a strain having lost the plasmid. PCR and analysis using a DNA sequencer were further carried out to isolate one strain from which the start to stop codons of the minE structural gene on the chromosome were deleted. In this manner, a minE gene-deleted strain was obtained.

(Production Example 2) Preparation of minC Gene Expression-Enhanced Strain

First, a minC gene expression plasmid pCUP2-PA-minC was prepared. The preparation was done as follows. PCR using a synthetic oligo DNA was carried out to obtain a DNA fragment (SEQ ID NO: 17) having a promotor sequence and a minC gene sequence. The DNA fragment was digested by restriction enzymes MunI and SpeI, and the resulting DNA fragment was joined to a plasmid vector pCUP2 which is described in WO 2007/049716 and which was cleaved by MunI and SpeI. Thus, the minC gene expression plasmid pCUP2-PA-minC was obtained.

Subsequently, the minC gene expression plasmid pCUP2-PA-minC was introduced into the KNK-005 stain to obtain a minC gene expression-enhanced strain. The introduction of the plasmid vector into the cells was accomplished by electroporation. The gene introduction device used was Gene Pulser manufactured by Bio-Rad Laboratories, Inc., and the cuvette used was a 0.2-cm-gap cuvette also manufactured by Bio-Rad Laboratories, Inc. The cuvette was charged with 400 μl of competent cells and 20 μl of an expression vector and set on the pulse device, by which electric pulse was applied to the contents of the cuvette at a capacitance of 25 μF, a voltage of 1.5 kV, and a resistance value of 800Ω. After the pulse application, the fluid in the cuvette was subjected to shake culture on Nutrient Broth (manufactured by Difco Laboratories) at 30° C. for 3 hours and then to culture on a selection plate (Nutrient Agar manufactured by Difco Laboratories, containing 100 mg/L kanamycin) at 30° C. for 2 days. The minC gene expression-enhanced strain thus grown was collected.

(Production Example 3) Preparation of minD Gene Expression-Enhanced Strain

First, a minD gene expression plasmid pCUP2-PA-minD was prepared. The preparation was done as follows.

PCR using a synthetic oligo DNA was carried out to obtain a DNA fragment (SEQ ID NO: 18) having a promoter sequence and a minD gene sequence. The DNA fragment was digested by restriction enzymes MunI and SpeI, and the resulting DNA fragment was joined to a plasmid vector pCUP2 which is described in WO 2007/049716 and which was cleaved by MunI and SpeI. Thus, the minD gene expression plasmid pCUP2-PA-minD was obtained.

Subsequently, the minD gene expression plasmid pCUP2-PA-minD was introduced into the KNK-005 strain in the same manner as the plasmid pCUP2-PA-minC was introduced in Production Example 2. Thus, a minD gene expression-enhanced strain was obtained.

(Production Example 4) Preparation of minCD Gene Expression-Enhanced Strain

First, a minCD gene expression plasmid pCUP2-PA-minCD was prepared. The preparation was done as follows.

PCR using a synthetic oligo DNA was carried out to obtain a DNA fragment (SEQ ID NO: 19) having a promoter sequence and a minCD gene sequence. The DNA fragment was digested by restriction enzymes MunI and SpeI, and the resulting DNA fragment was joined to a plasmid vector pCUP2 which is described in WO 2007/049716 and which was cleaved by MunI and SpeI. Thus, the minCD gene expression plasmid pCUP2-PA-minCD was obtained.

Subsequently, the minCD gene expression plasmid pCUP2-PA-minCD was introduced into the KNK-005 strain in the same manner as the plasmid pCUP2-PA-minC was introduced in Production Example 2. Thus, a minCD gene expression-enhanced strain was obtained.

(Production Example 5) Preparation of minD Gene Expression-Enhanced and minE Gene-Deleted Strain The minD gene expression plasmid pCUP2-PA-minD prepared in Production Example 3 was introduced into the minE gene-deleted strain prepared in Production Example 1 in the same manner as the plasmid pCUP2-PA-minC was introduced into the KNK-005 strain in Production Example 2. Thus, a minD gene expression-enhanced and minE gene-deleted strain was obtained.

(Production Example 6) Preparation of minCDE Gene Expression-Enhanced Expression First, a minCDE gene expression plasmid pCUP2-PA-minCDE was prepared. The preparation was done as follows.

PCR using a synthetic oligo DNA was carried out to obtain a DNA fragment (SEQ ID NO: 20) having a promoter sequence and a minCDE gene sequence. The DNA fragment was digested by restriction enzymes MunI and SpeI, and the resulting DNA fragment was joined to a plasmid vector pCUP2 which is described in WO 2007/049716 and which was cleaved by MunI and SpeI. Thus, the minCDE gene expression plasmid pCUP2-PA-minCDE was obtained.

Subsequently, the minCDE gene expression plasmid pCUP2-PA-minCDE was introduced into the KNK-005 strain in the same manner as the plasmid pCUP2-PA-minC was introduced in Production Example 2. Thus, a minCDE gene expression-enhanced strain was obtained.

(Production Example 7) Preparation of minCD Gene Expression-Enhanced and minE Gene-Deleted Strain The minCD gene expression plasmid pCUP2-PA-minCD prepared in Production Example 4 was introduced into the minE gene-deleted strain prepared in Production Example 1 in the same manner as the plasmid pCUP2-PA-minC was introduced into the KNK-005 strain in Production Example 2. Thus, a minCD gene expression-enhanced and minE gene-deleted strain was obtained.

(Comparative Example 1) PHA Production by KNK-005 Strain

Culture examination using the KNK-005 strain was conducted under the conditions described below.

Culture Media

The seed culture medium was composed of 1 w/v % Meat-extract, 1 w/v % Bacto-Tryptone, 0.2 w/v % Yeast-extract, 0.9 w/v % $Na_2HPO_4 \cdot 12H_2O$, and 0.15 w/v % $KH_2PO_4$ (pH=6.8). The preculture medium was composed of 1.1 w/v % $Na_2HPO_4 \cdot 12H_2O$, 0.19 w/v % $KH_2PO_4$, 1.29 w/v % $(NH_4)_2SO_4$, 0.1 w/v % $MgSO_4 \cdot 7H_2O$, 2.5 w/v % palm olein oil, and 0.5 v/v % trace metal salt solution (solution of 1.6 w/v % $FeCl_3 \cdot 6H_2O$, 1 w/v % $CaCl_2 \cdot 2H_2O$, 0.02 w/v % $CoCl_2 \cdot 6H_2O$, 0.016 w/v % $CuSO_4 \cdot 5H_2O$, and 0.012 w/v % $NiCl_2 \cdot 6H_2O$ in 0.1N hydrochloric acid). Palm olein oil was added as a carbon source in a concentration of 10 g/L at one time. The PHA production culture medium was composed of 0.385 w/v % $Na_2HPO_4 \cdot 12H_2O$, 0.067 w/v % $KH_2PO_4$, 0.291 w/v % $(NH_4)_2SO_4$, 0.1 w/v % $MgSO4 \cdot 7H_2O$, and 0.5 v/v % trace metal salt solution (solution of 1.6 w/v % $FeCl_3 \cdot 6H_2O$, 1 w/v % $CaCl_2 \cdot 2H_2O$, 0.02 w/v % $CoCl_2 \cdot 6H_2O$, 0.016 w/v % $CuSO_4 \cdot 5H_2O$, and 0.012 w/v % $NiCl_2 \cdot 6H_2O$ in 0.1N hydrochloric acid).

Method of Measuring Accumulated PHA Percentage

The accumulated PHA percentage was measured as follows. The microorganism was collected from the culture fluid by centrifugation. The collected microorganism was washed with ethanol and freeze-dried to give a dried microorganism, the weight of which was measured. To 1 g of the dried microorganism was added 100 ml of chloroform, and the microorganism in chloroform was stirred at room temperature for a day to extract a PHA from the microorganism. The residual microorganism was removed by filtration, and the filtrate was concentrated using an evaporator to a total volume of 30 ml. To the concentrate was slowly added 90 ml of hexane, and the mixture was left for 1 hour under gentle stirring. The PHA precipitated was collected by filtration and vacuum-dried at 50° C. for 3 hours. The weight of the dried PHA was measured, and the percentage of the accumulated PHA to the dried microorganism was calculated.

Method of Measuring Cell Size

The cell size was measured as follows. After the culture, the culture fluid was treated at 65° C. for 60 minutes to inactivate the microbial cells. The treated fluid was analyzed with a laser diffraction-scattering particle size distribution analyzer (Microtrac MT3300EXII) to measure the mean volume diameter (MV) of the cells. The measurement was conducted using standard settings (Permeability: Transparent, Particle refractive index: 1.81, Particle shape: Non-spherical, Solvent refractive index: 1.333).

Method of Measuring PHA Particle Size

The PHA particle size was measured as follows. After the culture, the culture fluid was treated at 65° C. for 60 minutes to inactivate the microbial cells. The culture fluid was diluted to 150 times the original volume with a 3.3 w/v % aqueous solution of sodium dodecyl sulfate, and subjected to ultrasonic disintegration to obtain a liquid containing the extracted PHA. The ultrasonic disintegration was conducted using Ultrasonic Homogenizer UH-600 manufactured by SMT Co., Ltd. and consisted of four repetitions of ultrasonic stirring performed at a maximum output for 40 seconds. The resulting liquid containing the extracted PHA was analyzed with a laser diffraction-scattering particle size distribution analyzer (Microtrac MT3300EXII) to measure the mean volume diameter (MV) of the PHA particles. The measurement was conducted using standard settings (Permeability: Transparent, Particle refractive index: 1.81, Particle shape: Non-spherical, Solvent refractive index: 1.333).

Microscopic Observation of Cells

Microscopic observation of the cells was conducted as follows. After the culture, the culture fluid was diluted as appropriate. The dilution was placed and dried on a glass slide, and then the cells were stained with fuchsin. The stained cells were observed with an optical microscope.

PHA Production Culture

PHA production culture was performed as follows. First, a glycerol stock (50 μl) of the KNK-005 strain was inoculated into the seed culture medium (10 ml) and cultured for 24 hours to accomplish seed culture. Subsequently, the seed culture fluid was inoculated at a concentration of 1.0 v/v % into a 3 L jar fermenter (MDL-300, manufactured by B. E. Marubishi Co., Ltd.) containing 1.8 L of the preculture medium. The fermenter was operated at a culture temperature of 33° C., a stirring speed of 500 rpm, and an aeration of 1.8 L/min, and the preculture was conducted for 28 hours during which the pH was controlled between 6.7 and 6.8. For the pH control, a 14% aqueous solution of ammonium hydroxide was used.

Next, the preculture fluid was inoculated at a concentration of 5.0 v/v % into a 5 L jar fermenter (MDS-U50, manufactured by B. E. Marubishi Co., Ltd.) containing 2.5 L of the PHA production culture medium. The fermenter was operated at a culture temperature of 33° C., a stirring speed of 420 rpm, and an aeration of 2.1 L/min, and the pH was controlled between 6.7 and 6.8. For the pH control, a 25% aqueous solution of ammonium hydroxide was used. The carbon source was added intermittently. Palm olein oil was used as the carbon source. The culture was continued until the accumulated PHA percentage reached around 90%. The accumulated PHA percentage, the cell size, and the PHA particle size were measured as previously described. The results are listed in Table 1. An image taken by the microscopic cell observation conducted as previously described is shown in FIG. 1.

(Comparative Example 2) PHA Production by minE Gene-Deleted Strain

Figure 2:
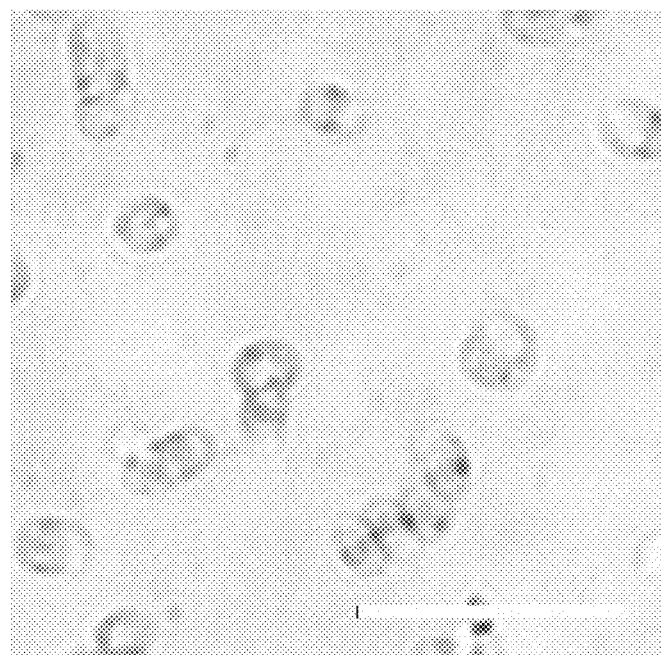
FIG. 2 is a microscope image of a cultured minE gene-deleted strain (Comparative Example 2).

Culture examination using the minE gene-deleted strain was conducted under the same conditions as the culture examination in Comparative Example 1. The measurement results of the accumulated PHA percentage, the cell size, and the PHA particle size are listed in Table 1. An image taken by the microscopic cell observation conducted as previously described is shown in FIG. 2.

The results of the culture examination revealed that the cell size of the minE gene-deleted strain was little different from that of the KNK-005 strain which was a parent strain.

Figure 3:
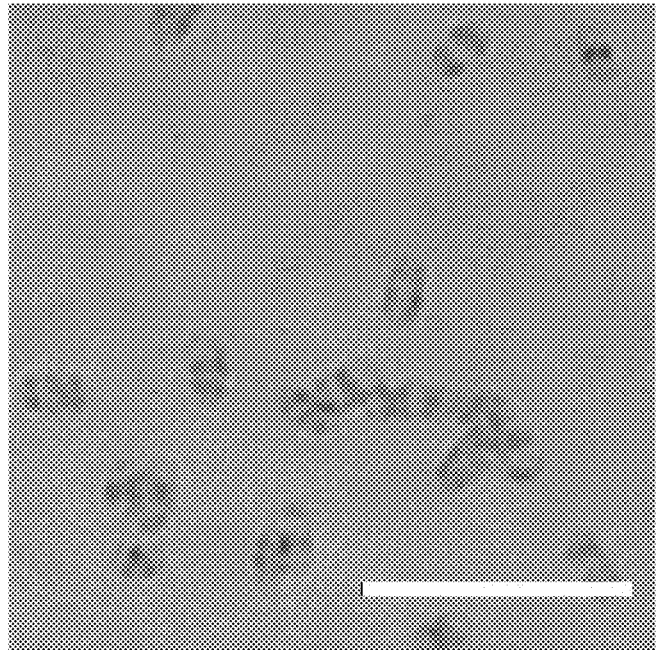
FIG. 3 is a microscope image of a cultured minC gene expression-enhanced strain (Comparative Example 3).

(Comparative Example 3) PHA Production by minC Gene Expression-Enhanced Strain Culture examination using the minC gene expression-enhanced strain was conducted under the same conditions as the culture examination in Comparative Example 1. The measurement results of the accumulated PHA percentage, the cell size, and the PHA particle size are listed in Table 1. An image taken by the microscopic cell observation conducted as previously described is shown in FIG. 3.

The results of the culture examination revealed that the cell size of the minC gene expression-enhanced strain was smaller than that of the KNK-005 strain which was a parent strain. Additionally, the PHA productivity of the minC gene expression-enhanced strain was considerably low, and the accumulated PHA percentage was only 83% despite the culture time being longer than in Comparative Example 1.

Figure 4:
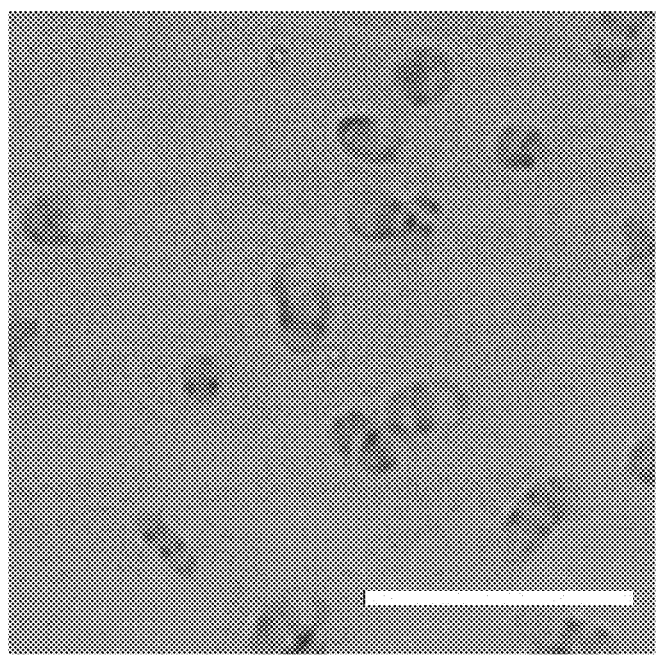
FIG. 4 is a microscope image of a cultured minD gene expression-enhanced and minE gene-deleted strain (Comparative Example 4).

(Comparative Example 4) PHA Production by minD Gene Expression-Enhanced and minE Gene-Deleted Strain Culture examination using the minD gene expression-enhanced and minE gene-deleted strain was conducted under the same conditions as the culture examination in Comparative Example 1. The measurement results of the accumulated PHA percentage, the cell size, and the PHA particle size are listed in Table 1. An image taken by the microscopic cell observation conducted as previously described is shown in FIG. 4.

The results of the culture examination revealed that the cell size of the minD gene expression-enhanced and minE gene-deleted strain was little different from that of the KNK-005 strain which was a parent strain.

(Example 1) PHA Production by minD Gene Expression-Enhanced Strain

Figure 5:
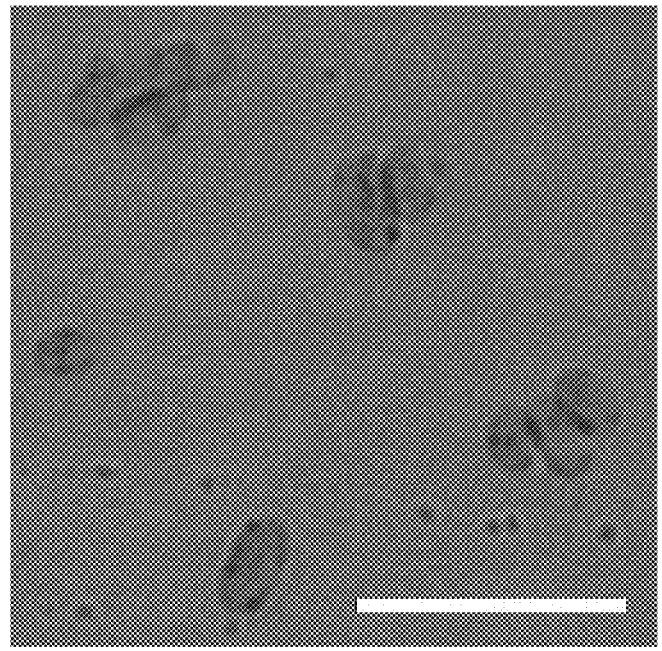
FIG. 5 is a microscope image of a cultured minD gene expression-enhanced strain (Example 1).

Culture examination using the minD gene expression-enhanced strain was conducted under the same conditions as the culture examination in Comparative Example 1. The measurement results of the accumulated PHA percentage, the cell size, and the PHA particle size are listed in Table 1. An image taken by the microscopic cell observation conducted as previously described is shown in FIG. 5.

The results of the culture examination revealed that the cell size of the minD gene expression-enhanced strain was more than 10% above that of the KNK-005 strain which was a parent strain. Additionally, the PHA productivity was comparable to that of the KNK-005 strain.

(Example 2) PHA Production by minCD Gene Expression-Enhanced Strain

Figure 6:
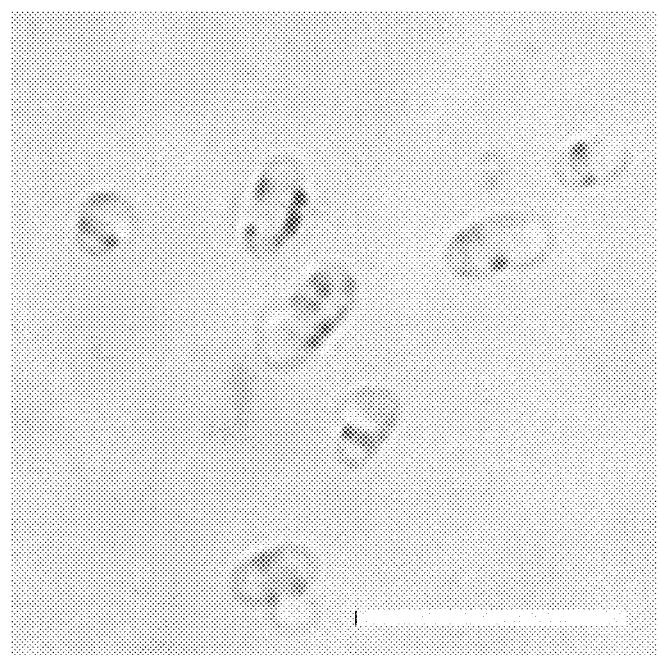
FIG. 6 is a microscope image of a cultured minCD gene expression-enhanced strain (Example 2).

Culture examination using the minCD gene expression-enhanced strain was conducted under the same conditions as the culture examination in Comparative Example 1. The measurement results of the accumulated PHA percentage, the cell size, and the PHA particle size are listed in Table 1. An image taken by the microscopic cell observation conducted as previously described is shown in FIG. 6.

The results of the culture examination revealed that the cell size of the minCD gene expression-enhanced strain was more than 15% above that of the KNK-005 strain which was a parent strain. Additionally, the PHA productivity was comparable to that of the KNK-005 strain. The particle size of the PHA produced by the minCD gene expression-enhanced strain was greater than the particle size of the PHA produced by the KNK-005 strain.

(Example 3) PHA Production by minCDE Gene Expression-Enhanced Strain

Figure 7:
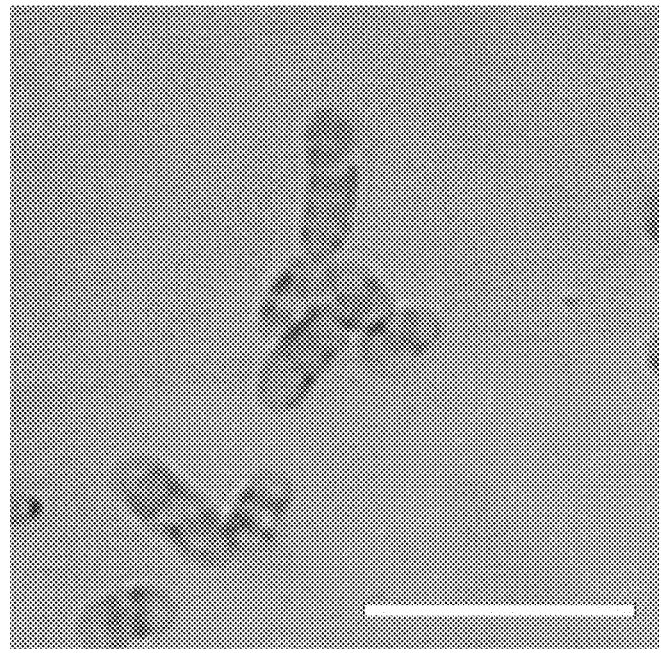
FIG. 7 is a microscope image of a cultured minCDE gene expression-enhanced strain (Example 3).

Culture examination using the minCDE gene expression-enhanced strain was conducted under the same conditions as the culture examination in Comparative Example 1. The measurement results of the accumulated PHA percentage, the cell size, and the PHA particle size are listed in Table 1. An image taken by the microscopic cell observation conducted as previously described is shown in FIG. 7.

The results of the culture examination revealed that the cell size of the minCDE gene expression-enhanced strain was more than 20% above that of the KNK-005 strain which was a parent strain. Additionally, the particle size of the PHA produced by the minCDE gene expression-enhanced strain was greater than the particle size of the PHA produced by the KNK-005 strain.

Figure 8:
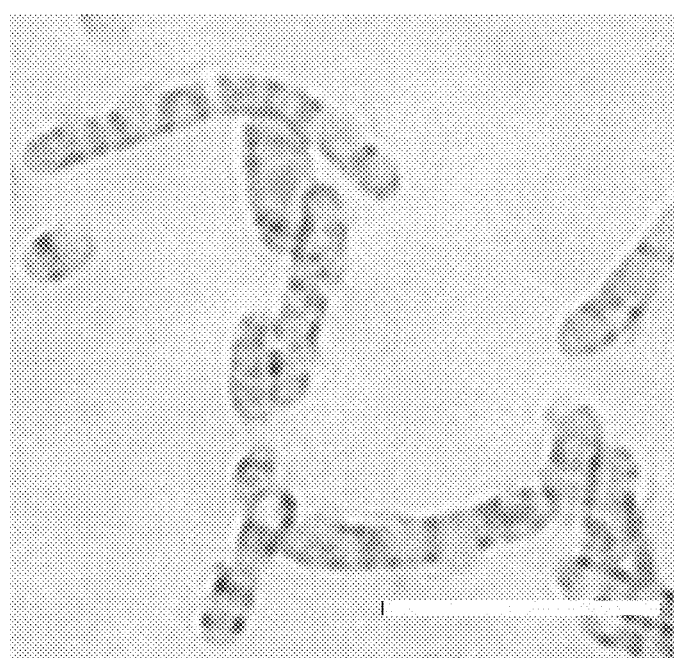
FIG. 8 is a microscope image of a cultured minCD gene expression-enhanced and minE gene-deleted strain (Example 4).

(Example 4) PHA Production by minCD Gene Expression-Enhanced and minE Gene-Deleted Strain Culture examination using the minCD gene expression-enhanced and minE gene-deleted strain was conducted under the same conditions as the culture examination in Comparative Example 1. The measurement results of the accumulated PHA percentage, the cell size, and the PHA particle size are listed in Table 1. An image taken by the microscopic cell observation conducted as previously described is shown in FIG. 8.

The results of the culture examination revealed that the cell size of the minCD gene expression-enhanced and minE gene-deleted strain was more than 55% or more above that of the KNK-005 strain which was a parent strain. Additionally, the PHA productivity was almost comparable to that of the KNK-005 strain.

The PHA produced in the culture examinations in Comparative Examples and Examples was found to be PHBH by HPLC analysis.

TABLE 1

| Strain | | Percentage of accumulated PHA to dried microorganism (%) | Cell size ($\mu$m) | PHA particle size ($\mu$m) |
|---|---|---|---|---|
| Comp. Example 1 | KNK-005 strain | 90 | 1.89 | 1.74 |
| Comp. Example 2 | minE gene-deleted strain | 90 | 1.93 | 1.72 |
| Comp. Example 3 | minC gene expression-enhanced strain | 83 | 1.58 | 1.34 |
| Comp. Example 4 | minD gene expression-enhanced and minE gene-deleted strain | 88 | 1.94 | 1.71 |
| Example 1 | minD gene expression-enhanced strain | 90 | 2.09 | 1.78 |
| Example 2 | minCD gene expression-enhanced strain | 90 | 2.24 | 1.94 |
| Example 3 | minCDE gene expression-enhanced strain | 90 | 2.34 | 1.87 |
| Example 4 | minCD gene expression-enhanced and minE gene-deleted strain | 87 | 3.00 | 1.73 |

The invention claimed is:

1. A transformed microorganism, belonging to the genus *Cupriavidus*, and comprising a polyhydroxyalkanoate synthase gene, wherein expression of a minC gene and a minD gene is enhanced as compared to a wild strain of the microorganism, wherein the minC gene is a gene having a nucleotide sequence that encodes a polypeptide comprising the amino acid sequence of SEQ ID NO: 1, or a polypeptide comprising an amino acid sequence that is at least 90% homologous to the amino acid sequence of SEQ ID NO: 1, the minD gene is a gene having a nucleotide sequence that encodes a polypeptide comprising the amino acid sequence of SEQ ID NO: 2, or a polypeptide comprising an amino acid sequence that is at least 90% homologous to the amino acid sequence of SEQ ID NO: 2, and the polyhydroxyalkanoate synthase gene is a gene having a nucleotide sequence that encodes a polypeptide comprising the amino acid sequence of SEQ ID NOS: 4, 5, 6, 7, or 8, or a polypeptide having polyhydroxyalkanoate synthase activity and comprising an amino acid sequence that is at least 90% homologous to the amino acid sequence of SEQ ID NOS: 4, 5, 6, 7, or 8, and a size of microbial cells of the transformed microorganism that accumulates polyhydroxyalkanoate is larger compared to a size of microbial cells of the wild strain that accumulates the polyhydroxyalkanoate, and the transformed microorganism accumulates larger-size particles of the polyhydroxyalkanoate compared to the wild strain.

2. The transformed microorganism according to claim 1, wherein expression of a minE gene is enhanced as compared to a wild strain of the microorganism,
wherein the minE gene is a gene having a nucleotide sequence that encodes a polypeptide comprising the amino acid sequence of SEQ ID NO: 3, or a polypeptide comprising an amino acid sequence that is at least 90% homologous to the amino acid sequence of SEQ ID NO: 3.

3. The transformed microorganism according to claim 2, which is transformed *Cupriavidus necator*.

4. A method of producing a polyhydroxyalkanoate, comprising culturing the transformed microorganism of claim 2 in the presence of a carbon source.

5. The method according to claim 4, wherein the carbon source comprises an oil or a fatty acid.

6. The method according to claim 4, wherein the carbon source comprises a sugar.

7. The method according to claim 4, wherein the carbon source contains comprises carbon dioxide.

8. The method according to claim 4, wherein the polyhydroxyalkanoate is a copolymer of at least two hydroxy alkanoates.

9. The method according to claim 8, wherein the polyhydroxyalkanoate is a copolymer comprising 3-hydroxyhexanoate as a monomer unit.

10. The method according to claim 9, wherein the polyhydroxyalkanoate is a copolymer of 3-hydroxybutyrate and 3-hydroxyhexanoate.

11. The transformed microorganism according to claim 1, which is transformed *Cupriavidus necator*.

12. A method of producing a polyhydroxyalkanoate, comprising culturing the transformed microorganism of claim 1 in the presence of a carbon source.

13. The method according to claim 12, wherein the carbon source comprises an oil or a fatty acid.

14. The method according to claim 12, wherein the carbon source comprises a sugar.

15. The method according to claim 12, wherein the carbon source comprises carbon dioxide.

16. The method according to claim 12, wherein the polyhydroxyalkanoate is a copolymer of at last two hydroxyalkanoates.

17. The method according to claim 16, wherein the polyhydroxyalkanoate is a copolymer comprising 3-hydroxyhexanoate as a monomer unit.

18. The method according to claim 17, wherein the polyhydroxyalkanoate is a copolymer of 3-hydroxybutyrate and 3-hydroxyhexanoate.

19. The transformed microorganism according to claim 1, wherein the size of microbial cells of the transformed microorganism that accumulates the polyhydroxyalkanoate is at least 2.24 µm, and the size of polyhydroxyalkanoate particles that are accumulated by the transformed microorganism is at least 1.94 µm.

20. The transformed microorganism according to claim 2, wherein the size of microbial cells of the transformed microorganism that accumulates the polyhydroxyalkanoate is at least 2.34 µm, and the size of polyhydroxyalkanoate particles that are accumulated by the transformed microorganism is at least 1.87 µm.

* * * * *

SEQUENCE LISTING

<160> NUMBER OF SEQ ID NOS: 20

<210> SEQ ID NO 1
<211> LENGTH: 270
<212> TYPE: PRT
<213> ORGANISM: Cupriavidus necator

<400> SEQUENCE: 1

Met Ser Gln Lys Lys Ser Pro Arg Phe Glu Leu Arg Ser Gly Asn Val
1               5                   10                  15

Asp Ala Leu Leu Leu Ala Leu Gln Thr Ala Asp Met Ala Ala Leu Arg
            20                  25                  30

Asp Asp Leu Leu Ala Arg Phe Glu Ala Thr Pro Asp Phe Phe Ser Asn
        35                  40                  45

Asp Val Ile Ala Leu Asp Leu Arg Ala Leu Glu Asp Asp Ser Glu Val
    50                  55                  60

```
Ala Leu Gly Thr Val Ile Glu Thr Leu Ala Thr Leu Arg Ala Arg Ala
 65                  70                  75                  80

Ile Gly Val Val Ala Arg Pro Gly Gln Arg Glu Trp Ala Glu Arg Phe
                 85                  90                  95

Gly Leu Pro Leu Leu Asp Ser Gln Ala Arg Arg Gly Ser Gly Ala Asp
            100                 105                 110

Arg Ala Thr Asp Arg Ala Ala Glu Ala Arg Ala Ala Ala Ala Ala Glu
        115                 120                 125

Gln Ala Ala Asp Gln Ala Ala Arg Glu Glu Ser Ile Arg Ala Ala
130                 135                 140

Ala Gln Ala Thr Thr Asp Ala Ala Val Ala Ala Ile Arg Gln Thr
145                 150                 155                 160

Gln Thr Met Leu Ile Asp Lys Pro Leu Arg Ser Gly Gln Gln Val Tyr
                165                 170                 175

Ala Gln Gly Asp Val Val Ile Leu Asp Val Val Ser Tyr Gly Ala Glu
            180                 185                 190

Val Ile Ala Glu Gly Asn Ile His Ile Tyr Ala Pro Leu Arg Gly Arg
        195                 200                 205

Ala Leu Ala Gly Val Lys Gly Asn Thr Gly Ala Arg Ile Phe Ser Thr
    210                 215                 220

Cys Met Glu Pro Glu Leu Ile Ser Ile Ala Gly Ile Tyr Arg Thr Ala
225                 230                 235                 240

Glu Gln Thr Leu Pro Ala Asp Val Leu Gly Lys Thr Ala Gln Val Arg
                245                 250                 255

Leu Ala Asp Glu Lys Leu Ile Leu Glu Ala Leu Arg Leu Lys
            260                 265                 270

<210> SEQ ID NO 2
<211> LENGTH: 271
<212> TYPE: PRT
<213> ORGANISM: Cupriavidus necator

<400> SEQUENCE: 2

Met Ala Lys Ile Ile Val Val Thr Ser Gly Lys Gly Gly Val Gly Lys
1               5                   10                  15

Thr Thr Thr Ser Ala Ser Phe Ala Ala Gly Leu Ala Leu Arg Gly His
                20                  25                  30

Lys Thr Ala Val Ile Asp Phe Asp Val Gly Leu Arg Asn Leu Asp Leu
            35                  40                  45

Ile Met Gly Cys Glu Arg Arg Val Val Tyr Asp Leu Ile Asn Val Val
        50                  55                  60

Gln Gly Glu Ala Asn Leu Arg Gln Ala Leu Ile Lys Asp Lys Lys Cys
65                  70                  75                  80

Glu Asn Leu Phe Ile Leu Pro Ala Ser Gln Thr Arg Asp Lys Asp Ala
                85                  90                  95

Leu Thr Arg Glu Gly Val Glu Lys Val Ile Asn Gly Leu Ile Glu Met
            100                 105                 110

Asp Phe Glu Phe Ile Ile Cys Asp Ser Pro Ala Gly Ile Glu Ser Gly
        115                 120                 125

Ala Leu Met Ala Met Tyr Phe Ala Asp Glu Ala Leu Ile Val Thr Asn
    130                 135                 140

Pro Glu Val Ser Ser Val Arg Asp Ser Asp Arg Ile Leu Gly Ile Leu
145                 150                 155                 160

Ala Ser Lys Thr Lys Arg Ala Ser Glu Gly Gly Asp Pro Ile Lys Glu
                165                 170                 175
```

```
His Leu Leu Ile Thr Arg Tyr Asn Pro Lys Arg Val His Gly Gly Glu
            180                 185                 190

Met Leu Ser Leu Thr Asp Ile Gln Glu Ile Leu Arg Ile Lys Leu Ile
            195                 200                 205

Gly Val Val Pro Glu Ser Glu Ala Val Leu His Ala Ser Asn Gln Gly
    210                 215                 220

Thr Pro Ala Ile His Leu Glu Gly Ser Asp Val Ala Asp Ala Tyr Gly
225                 230                 235                 240

Asp Val Val Asp Arg Phe Leu Gly Lys Asp Lys Pro Met Arg Phe Thr
                245                 250                 255

Asp Tyr Gln Lys Pro Gly Leu Leu Ser Arg Ile Phe Gly Asn Lys
                260                 265                 270

<210> SEQ ID NO 3
<211> LENGTH: 84
<212> TYPE: PRT
<213> ORGANISM: Cupriavidus necator

<400> SEQUENCE: 3

Met Ser Ile Leu Ser Phe Leu Leu Gly Glu Lys Lys Ser Ala Ser
1               5                   10                  15

Val Ala Lys Glu Arg Leu Gln Ile Ile Leu Ala His Glu Arg Thr Gly
            20                  25                  30

His Ser Ala Pro Ala Asp Tyr Leu Pro Ala Leu Gln Arg Glu Leu Val
        35                  40                  45

Ala Val Ile Ser Lys Tyr Val Lys Ile Gly Asp Gln Asp Leu Arg Val
    50                  55                  60

Ser Leu Glu Arg Gln Asp Asn Leu Glu Val Leu Glu Val Lys Ile Glu
65                  70                  75                  80

Ile Pro Gln Asn

<210> SEQ ID NO 4
<211> LENGTH: 589
<212> TYPE: PRT
<213> ORGANISM: Cupriavidus necator

<400> SEQUENCE: 4

Met Ala Thr Gly Lys Gly Ala Ala Ala Ser Thr Gln Glu Gly Lys Ser
1               5                   10                  15

Gln Pro Phe Lys Val Thr Pro Gly Pro Phe Asp Pro Ala Thr Trp Leu
            20                  25                  30

Glu Trp Ser Arg Gln Trp Gln Gly Thr Glu Gly Asn Gly His Ala Ala
        35                  40                  45

Ala Ser Gly Ile Pro Gly Leu Asp Ala Leu Ala Gly Val Lys Ile Ala
    50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
        115                 120                 125

Glu Leu Ala Asp Ala Val Glu Ala Asp Ala Lys Thr Arg Gln Arg Ile
    130                 135                 140
```

-continued

```
Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
            180                 185                 190

Gly Lys Ile Ser Gln Thr Asp Glu Ser Ala Phe Glu Val Gly Arg Asn
        195                 200                 205

Val Ala Val Thr Glu Gly Ala Val Val Phe Glu Asn Glu Tyr Phe Gln
    210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
                245                 250                 255

Pro Glu Ser Ser Leu Val Arg His Val Val Glu Gln Gly His Thr Val
                260                 265                 270

Phe Leu Val Ser Trp Arg Asn Pro Asp Ala Ser Met Ala Gly Ser Thr
            275                 280                 285

Trp Asp Asp Tyr Ile Glu His Ala Ala Ile Arg Ala Ile Glu Val Ala
        290                 295                 300

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
                340                 345                 350

Ala Asp Thr Gly Ile Leu Asp Val Phe Val Asp Glu Gly His Val Gln
            355                 360                 365

Leu Arg Glu Ala Thr Leu Gly Gly Ala Gly Ala Pro Cys Ala Leu
        370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
                420                 425                 430

Pro Gly Pro Trp Tyr Cys Trp Tyr Leu Arg His Thr Tyr Leu Gln Asn
            435                 440                 445

Glu Leu Lys Val Pro Gly Lys Leu Thr Val Cys Gly Val Pro Val Asp
        450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
                500                 505                 510

Ile Asn Pro Pro Ala Lys Asn Lys Arg Ser His Trp Thr Asn Asp Ala
            515                 520                 525

Leu Pro Glu Ser Pro Gln Gln Trp Leu Ala Gly Ala Ile Glu His His
        530                 535                 540

Gly Ser Trp Trp Pro Asp Trp Thr Ala Trp Leu Ala Gly Gln Ala Gly
545                 550                 555                 560

Ala Lys Arg Ala Ala Pro Ala Asn Tyr Gly Asn Ala Arg Tyr Arg Ala
```

Ile Glu Pro Ala Pro Gly Arg Tyr Val Lys Ala Lys Ala
            580                 585

<210> SEQ ID NO 5
<211> LENGTH: 594
<212> TYPE: PRT
<213> ORGANISM: Aeromonas caviae

<400> SEQUENCE: 5

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

```
Phe Ser Gln Pro Gly Glu Leu Gly Ile Phe Ile His Glu Pro Ile Ile
            355                 360                 365
Ala Ala Leu Glu Ala Gln Asn Glu Ala Lys Gly Ile Met Asp Gly Arg
        370                 375                 380
Gln Leu Ala Val Ser Phe Ser Leu Leu Arg Glu Asn Ser Leu Tyr Trp
385                 390                 395                 400
Asn Tyr Tyr Ile Asp Ser Tyr Leu Lys Gly Gln Ser Pro Val Ala Phe
                405                 410                 415
Asp Leu Leu His Trp Asn Ser Asp Ser Thr Asn Val Ala Gly Lys Thr
            420                 425                 430
His Asn Ser Leu Leu Arg Arg Leu Tyr Leu Glu Asn Gln Leu Val Lys
        435                 440                 445
Gly Glu Leu Lys Ile Arg Asn Thr Arg Ile Asp Leu Gly Lys Val Lys
    450                 455                 460
Thr Pro Val Leu Leu Val Ser Ala Val Asp Asp His Ile Ala Leu Trp
465                 470                 475                 480
Gln Gly Thr Trp Gln Gly Met Lys Leu Phe Gly Gly Glu Gln Arg Phe
                485                 490                 495
Leu Leu Ala Glu Ser Gly His Ile Ala Gly Ile Ile Asn Pro Pro Ala
            500                 505                 510
Ala Asn Lys Tyr Gly Phe Trp His Asn Gly Ala Glu Ala Glu Ser Pro
        515                 520                 525
Glu Ser Trp Leu Ala Gly Ala Thr His Gln Gly Gly Ser Trp Trp Pro
    530                 535                 540
Glu Met Met Gly Phe Ile Gln Asn Arg Asp Glu Gly Ser Glu Pro Val
545                 550                 555                 560
Pro Ala Arg Val Pro Glu Gly Leu Ala Pro Ala Pro Gly His Tyr
                565                 570                 575
Val Lys Val Arg Leu Asn Pro Val Phe Ala Cys Pro Thr Glu Glu Asp
            580                 585                 590
Ala Ala

<210> SEQ ID NO 6
<211> LENGTH: 594
<212> TYPE: PRT
<213> ORGANISM: Aeromonas caviae

<400> SEQUENCE: 6

Met Ser Gln Pro Ser Tyr Gly Pro Leu Phe Glu Ala Leu Ala His Tyr
1               5                   10                  15
Asn Asp Lys Leu Leu Ala Met Ala Lys Ala Gln Thr Glu Arg Thr Ala
            20                  25                  30
Gln Ala Leu Leu Gln Thr Asn Leu Asp Asp Leu Gly Gln Val Leu Glu
        35                  40                  45
Gln Gly Ser Gln Gln Pro Trp Gln Leu Ile Gln Ala Gln Met Asn Trp
    50                  55                  60
Trp Gln Asp Gln Leu Lys Leu Met Gln His Thr Leu Leu Lys Ser Ala
65                  70                  75                  80
Gly Gln Pro Ser Glu Pro Val Ile Thr Pro Glu Arg Ser Asp Arg Arg
                85                  90                  95
Phe Lys Ala Glu Ala Trp Ser Glu Gln Pro Ile Tyr Asp Tyr Leu Lys
            100                 105                 110
Gln Ser Tyr Leu Leu Thr Ala Arg His Leu Leu Ala Ser Val Asp Ala
        115                 120                 125
```

```
Leu Glu Gly Val Pro Gln Lys Ser Arg Glu Arg Leu Arg Phe Phe Thr
130                 135                 140

Arg Gln Tyr Val Ser Ala Met Ala Pro Ser Asn Phe Leu Ala Thr Asn
145                 150                 155                 160

Pro Glu Leu Leu Lys Leu Thr Leu Glu Ser Gly Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
    370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
        515                 520                 525

Glu Ser Trp Leu Ala Gly Ala Thr His Gln Gly Gly Ser Trp Trp Pro
    530                 535                 540

Glu Met Met Gly Phe Ile Gln Asn Arg Asp Glu Gly Ser Glu Pro Val
```

```
                545                 550                 555                 560
Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
                580                 585                 590

Ala Ala

<210> SEQ ID NO 7
<211> LENGTH: 567
<212> TYPE: PRT
<213> ORGANISM: Chromobacterium sp.

<400> SEQUENCE: 7

Met Gln Gln Phe Val Asn Ser Leu Ser Leu Gly Gln Asp Gln Ser Asp
1               5                   10                  15

Ala Pro His Pro Leu Thr Gly Ala Trp Ser Gln Leu Met Ser Gln Thr
                20                  25                  30

Asn Gln Leu Leu Gln Leu Gln Ser Ser Leu Tyr Gln Gln Gln Leu Gly
            35                  40                  45

Leu Trp Thr Gln Phe Leu Gly Gln Thr Ala Gly Asn Asp Ala Ser Ala
        50                  55                  60

Pro Ser Ala Lys Pro Ser Asp Arg Arg Phe Ala Ser Pro Glu Trp Asp
65                  70                  75                  80

Glu His Pro Phe Tyr Ser Phe Leu Lys Gln Ser Tyr Leu Gln Thr Ser
                85                  90                  95

Lys Trp Met Met Glu Leu Val Asp Lys Thr Gln Ile Asp Glu Ser Ala
                100                 105                 110

Lys Asp Lys Leu Ser Phe Ala Thr Arg Gln Tyr Leu Asp Ala Met Ala
            115                 120                 125

Pro Ser Asn Phe Met Leu Thr Asn Pro Asp Val Val Lys Arg Ala Ile
    130                 135                 140

Glu Thr Gln Gly Glu Ser Leu Val Glu Gly Met Lys Asn Met Met Glu
145                 150                 155                 160

Asp Ile Gln Lys Gly His Ile Ser Met Ser Asp Glu Ser Lys Phe Gln
                165                 170                 175

Ile Gly Lys Asn Leu Val Val Thr Pro Gly Glu Val Val Phe Arg Asn
            180                 185                 190

Glu Leu Ile Glu Leu Ile Gln Tyr Thr Pro Thr Thr Glu Lys Val His
        195                 200                 205

Glu Lys Pro Leu Leu Phe Val Pro Pro Cys Ile Asn Lys Tyr Tyr Leu
    210                 215                 220

Met Asp Leu Gln Pro Asp Asn Ser Met Val Arg His Phe Val Gly Gln
225                 230                 235                 240

Gly Tyr Arg Val Phe Leu Val Ser Trp Arg Ser Ala Val Pro Glu Met
                245                 250                 255

Lys Asn Phe Thr Trp Glu Thr Tyr Ile Glu Lys Gly Val Phe Ala Ala
            260                 265                 270

Ala Glu Ala Val Gln Lys Ile Thr Lys Gln Pro Thr Met Asn Ala Leu
        275                 280                 285

Gly Phe Cys Val Gly Gly Val Ile Leu Thr Thr Ala Leu Cys Val Ala
    290                 295                 300

Gln Ala Lys Gly Leu Lys Tyr Phe Asp Ser Ala Thr Phe Met Thr Ser
305                 310                 315                 320

Leu Ile Asp His Ala Glu Pro Gly Glu Ile Ser Phe Phe Ile Asp Glu
```

```
                    325                 330                 335
Ala Leu Val Ala Ser Arg Glu Ala Lys Met Ala Ala Gly Gly Ile Ile
                340                 345                 350

Ser Gly Lys Glu Ile Gly Arg Thr Phe Ala Ser Leu Arg Ala Asn Asp
            355                 360                 365

Leu Val Trp Asn Tyr Val Asn Asn Tyr Leu Leu Gly Lys Thr Pro
        370                 375                 380

Ala Pro Phe Asp Leu Leu Tyr Trp Asn Asp Ala Val Asp Leu Pro
385                 390                 395                 400

Leu Pro Met His Thr Phe Met Leu Arg Gln Phe Tyr Ile Asn Asn Ala
                405                 410                 415

Leu Ile Thr Pro Gly Ala Ile Thr Leu Cys Gly Val Pro Ile Asp Ile
                420                 425                 430

Ser Lys Ile Asp Ile Pro Val Tyr Met Phe Ala Ala Arg Glu Asp His
                435                 440                 445

Ile Val Leu Trp Ser Ser Ala Tyr Ser Gly Leu Lys Tyr Leu Ser Gly
                450                 455                 460

Thr Pro Ser Arg Arg Phe Val Leu Gly Ala Ser Gly His Ile Ala Gly
465                 470                 475                 480

Ser Ile Asn Pro Val Thr Lys Asp Lys Arg Asn Tyr Trp Thr Asn Glu
                485                 490                 495

Gln Leu Pro Val Asn Pro Glu Glu Trp Leu Glu Gly Ala Gln Ser His
                500                 505                 510

Pro Gly Ser Trp Trp Lys Asp Trp Asp Ala Trp Leu Ala Pro Gln Ser
            515                 520                 525

Gly Lys Gln Val Pro Ala Pro Lys Met Leu Gly Ser Lys Glu Phe Pro
            530                 535                 540

Pro Leu Gln Pro Ala Pro Gly Ser Tyr Val Leu Ala Lys Ala Met Pro
545                 550                 555                 560

Pro Val Ala Ala Ala Leu Asn
                565

<210> SEQ ID NO 8
<211> LENGTH: 559
<212> TYPE: PRT
<213> ORGANISM: Pseudomonas sp.

<400> SEQUENCE: 8

Met Ser Asn Lys Asn Ser Asp Asp Leu Asn Arg Gln Ala Ser Glu Asn
1               5                   10                  15

Thr Leu Gly Leu Asn Pro Val Ile Gly Leu Arg Gly Lys Asp Leu Leu
                20                  25                  30

Thr Ser Ala Arg Met Val Leu Thr Gln Ala Ile Lys Gln Pro Ile His
            35                  40                  45

Ser Val Lys His Val Ala His Phe Gly Ile Glu Leu Lys Asn Val Met
        50                  55                  60

Phe Gly Lys Ser Lys Leu Gln Pro Glu Ser Asp Asp Arg Arg Phe Asn
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Gly Asn Ser Lys
            100                 105                 110

Leu Ser Glu Gln Asp Ile Asn Arg Ala His Phe Val Ile Thr Leu Met
        115                 120                 125
```

```
Thr Glu Ala Met Ala Pro Thr Asn Ser Ala Ala Asn Pro Ala Ala Val
            130                 135                 140

Lys Arg Phe Phe Glu Thr Gly Gly Lys Ser Leu Leu Asp Gly Leu Thr
145                 150                 155                 160

His Leu Ala Lys Asp Leu Val Asn Asn Gly Gly Met Pro Ser Gln Val
                165                 170                 175

Asp Met Gly Ala Phe Glu Val Gly Lys Ser Leu Gly Thr Thr Glu Gly
            180                 185                 190

Ala Val Val Phe Arg Asn Asp Val Leu Glu Leu Ile Gln Tyr Arg Pro
            195                 200                 205

Thr Thr Glu Gln Val His Glu Arg Pro Leu Leu Val Val Pro Pro Gln
210                 215                 220

Ile Asn Lys Phe Tyr Val Phe Asp Leu Ser Pro Asp Lys Ser Leu Ala
225                 230                 235                 240

Arg Phe Cys Leu Ser Asn Asn Gln Gln Thr Phe Ile Val Ser Trp Arg
                245                 250                 255

Asn Pro Thr Lys Ala Gln Arg Glu Trp Gly Leu Ser Tyr Ile Asp
                260                 265                 270

Ala Leu Lys Glu Ala Val Asp Val Val Ser Ala Ile Thr Gly Ser Lys
            275                 280                 285

Asp Ile Asn Met Leu Gly Ala Cys Ser Gly Gly Ile Thr Cys Thr Ala
            290                 295                 300

Leu Leu Gly His Tyr Ala Ala Leu Gly Glu Lys Lys Val Asn Ala Leu
305                 310                 315                 320

Thr Leu Leu Val Ser Val Leu Asp Thr Thr Leu Asp Ser Gln Val Ala
                325                 330                 335

Leu Phe Val Asp Glu Lys Thr Leu Glu Ala Ala Lys Arg His Ser Tyr
            340                 345                 350

Gln Ala Gly Val Leu Glu Gly Arg Asp Met Ala Lys Val Phe Ala Trp
            355                 360                 365

Met Arg Pro Asn Asp Leu Ile Trp Asn Tyr Trp Val Asn Asn Tyr Leu
370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Asn Asn Pro Leu Val Arg Ala Asn Ala Leu Glu Val Ser Gly Thr
                420                 425                 430

Pro Ile Asp Leu Lys Gln Val Thr Ala Asp Ile Tyr Ser Leu Ala Gly
            435                 440                 445

Thr Asn Asp His Ile Thr Pro Trp Lys Ser Cys Tyr Lys Ser Ala Gln
450                 455                 460

Leu Phe Gly Gly Lys Val Glu Phe Val Leu Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Asp Met Pro Ala Thr Ala Asn Glu Trp Gln Glu Asn Ser Thr
            500                 505                 510

Lys His Thr Asp Ser Trp Trp Leu His Trp Gln Ala Trp Gln Ala Glu
            515                 520                 525

Arg Ser Gly Lys Leu Lys Lys Ser Pro Thr Ser Leu Gly Asn Lys Ala
530                 535                 540

Tyr Pro Ser Gly Glu Ala Ala Pro Gly Thr Tyr Val His Glu Arg
```

<210> SEQ ID NO 9
<211> LENGTH: 29
<212> TYPE: DNA
<213> ORGANISM: Artificial Sequence
<220> FEATURE:
<223> OTHER INFORMATION: Artificial DNA

<400> SEQUENCE: 9
ttgacaatta atcatccggc tcgtataat                                    29

<210> SEQ ID NO 10
<211> LENGTH: 30
<212> TYPE: DNA
<213> ORGANISM: Escherichia coli

<400> SEQUENCE: 10
tttacacttt atgcttccgg ctcgtataat                                   30

<210> SEQ ID NO 11
<211> LENGTH: 30
<212> TYPE: DNA
<213> ORGANISM: Escherichia coli

<400> SEQUENCE: 11
ttgacaatta atcatcgaac tagttaacta                                   30

<210> SEQ ID NO 12
<211> LENGTH: 30
<212> TYPE: DNA
<213> ORGANISM: Escherichia coli

<400> SEQUENCE: 12
tttacacttt atgcttccgg ctcgtatgtt                                   30

<210> SEQ ID NO 13
<211> LENGTH: 30
<212> TYPE: DNA
<213> ORGANISM: Cupriavidus necator

<400> SEQUENCE: 13
ttgacagcgc gtgcgttgca aggcaacaat                                   30

<210> SEQ ID NO 14
<211> LENGTH: 231
<212> TYPE: DNA
<213> ORGANISM: Cupriavidus necator

<400> SEQUENCE: 14
tacgccgccc cctgaccagg aacgccgggc cagtcccggc gttttttttat tctatagcgc    60 aattaaccgc cgtcatattg cgtcaccatg attgccggat ggccgcggcg atcccttgct   120
ggaggccggt tccaagaaga tttaaagatg tcacggaatt gtcatacagg gagcatagag   180
ttcgtcttgt caaaaatttg tcattcccaa ccaatgttct ctggaggaca t            231

<210> SEQ ID NO 15
<211> LENGTH: 17
<212> TYPE: DNA
<213> ORGANISM: Cupriavidus necator

<400> SEQUENCE: 15
agagagacaa tcaaatc                                                 17

<210> SEQ ID NO 16
<211> LENGTH: 828
<212> TYPE: DNA
<213> ORGANISM: Artificial Sequence
<220> FEATURE:
<223> OTHER INFORMATION: Artificial DNA

<400> SEQUENCE: 16

| | | | | | | |
|---|---|---|---|---|---|---|
| ctatccattt | aaatagtgtc | gtcggtgcgc | gattcggacc | gcatcctggg | catcctggcc | 60 |
| tccaagacca | agcgcgccag | cgaaggcggc | gacccgatca | aggaacacct | gctgatcacc | 120 |
| cgctacaacc | ccaagcgtgt | gcatggcggc | gaaatgctgt | cgctgaccga | catccaggaa | 180 |
| atcctgcgca | tcaagctgat | cggcgtggtg | ccggagtctg | aagccgtgct | gcacgcctcg | 240 |
| aaccagggca | cgcccgccat | ccacctggaa | ggcagcgacg | tggccgacgc | ctatggcgac | 300 |
| gtggtggacc | gcttcctcgg | caaggacaag | ccgatgcgtt | tcaccgacta | ccagaagccg | 360 |
| ggtctgctct | cccgcatctt | cggcaacaag | taacggtcaa | ggagggctca | ccccggacgg | 420 |
| atcccggcgc | tgccggattc | gttcctcctc | cttcggtttt | cccgcacttc | ccgtctttcc | 480 |
| gccgaccgcg | gcgccgcttg | cgcgccgggg | tcggccggcc | ccgtcctcc | ccgccgcgat | 540 |
| tccccaccag | cccagtgtgc | aggccagctg | ccagcgctgc | cagaacgccc | caattcggaa | 600 |
| ttctgtagcg | gcgagacaac | ggatttgcac | caaaatcctg | cttgaaaggg | cagcttggcg | 660 |
| gagttttgtg | tccttgtagc | ttacgttttg | ttaaattttc | gcggcgtcta | caacgaaacg | 720 |
| tagacatcgt | ccccgccgtg | atccggcgga | gagaacagta | caagacagaa | aaggagcacc | 780 |
| atgaagaaat | cggccatcgt | cctcgcagcc | ggcaatttaa | atccgaat | | 828 |

<210> SEQ ID NO 17
<211> LENGTH: 1100
<212> TYPE: DNA
<213> ORGANISM: Artificial Sequence
<220> FEATURE:
<223> OTHER INFORMATION: Artificial DNA

<400> SEQUENCE: 17

| | | | | | | |
|---|---|---|---|---|---|---|
| aagggccaat | tgtacgccgc | ccctgacca | ggaacgccgg | gccagtcccg | gcgttttttt | 60 |
| attctatagc | gcaattaacc | gccgtcatat | tgcgtcacca | tgattgccgg | atggccgcgg | 120 |
| cgatcccttg | ctggaggccg | gttccaagaa | gatttaaaga | tgtcacggaa | ttgtcataca | 180 |
| gggagcatag | agttcgtctt | gtcaaaaatt | tgtcattccc | aaccaatgtt | ctctggagga | 240 |
| catatgtccc | agaagaaatc | gccacgcttc | gagctgcgca | gtggcaacgt | agacgccctc | 300 |
| cttctcgccc | tccagaccgc | cgacatggct | gcgctgcggg | atgacctcct | cgcccgcttt | 360 |
| gaagccaccc | ccgacttctt | ttccaatgac | gtgattgcgc | tggacctgcg | cgcgctggaa | 420 |
| gatgacagcg | aagtcgcgct | tggcaccgtg | atcgagacgc | tggccacgct | cagggcccgc | 480 |
| gccatcggcg | tggtggcccg | ccccggccag | cgcgagtggg | ccgagcgctt | cggcctgccg | 540 |
| ctgctggaca | gccaggcccg | ccgcggcagt | ggcgccgatc | gcgccaccga | ccgtgccgcc | 600 |
| gaggccaggg | ccgcagccgc | ggcggaacag | gccgcagccg | accaggccgc | gcgcgaggaa | 660 |
| tccatccgcg | ccgccgcgca | ggccaccacc | gacgccgccg | tggccgctgc | catccgccag | 720 |
| acccagacca | tgctgatcga | caagccgctt | cgctcgggcc | agcaggtcta | cgcgcagggc | 780 |
| gacgtggtca | tcctggacgt | ggtcagctac | ggcgccgagg | tgatcgccga | aggcaacatc | 840 |
| catatctatg | ccccgctgcg | cggccgtgcg | ctggcgggcg | tcaagggcaa | caccggcgcg | 900 |

| | |
|---|---|
| cgcattttca gcacgtgcat ggagcctgaa ctgatttcca tcgccggcat ctaccggacc | 960 |
| gcggagcaga cgcttccggc cgacgtgctc ggcaagaccg cccaggtgcg cctggccgat | 1020 |
| gaaaaactga tcctggaagc gctgcggctc aagtaacctg ccggcctggt tcaaccagtc | 1080 |
| ggcagccgac tagtggatcc | 1100 |

<210> SEQ ID NO 18
<211> LENGTH: 1103
<212> TYPE: DNA
<213> ORGANISM: Artificial Sequence
<220> FEATURE:
<223> OTHER INFORMATION: Artificial DNA

<400> SEQUENCE: 18

| | |
|---|---|
| aagggccaat tgtacgccgc ccctgacca ggaacgccgg ccagtcccg gcgttttttt | 60 |
| attctatagc gcaattaacc gccgtcatat tgcgtcacca tgattgccgg atggccgcgg | 120 |
| cgatcccttg ctggaggccg gttccaagaa gatttaaaga tgtcacggaa ttgtcataca | 180 |
| gggagcatag agttcgtctt gtcaaaaatt tgtcattccc aaccaatgtt ctctggagga | 240 |
| catatggcaa aaatcatcgt tgtgacctcc ggcaagggag gcgtcggcaa gaccaccacc | 300 |
| agcgccagct ttgccgccgg cctggccctg cgcggccaca agactgccgt gatcgacttc | 360 |
| gacgtcggcc tgcgcaacct tgacctgatc atgggttgcg agcgccgcgt ggtgtacgac | 420 |
| ctgatcaacg tggtgcaggg cgaagccaac ctgcgccagg cgctgatcaa ggacaagaag | 480 |
| tgcgagaacc tgttcatcct gccggcctcg cagacgcgcg acaaggacgc gctcacgcgc | 540 |
| gaaggcgtcg agaaggtcat caacggcctg atcgagatgg atttcgaatt catcatctgc | 600 |
| gactcgccgg ccggcatcga gtcgggcgcg ctgatggcga tgtacttcgc cgacgaggcg | 660 |
| ctgatcgtga ccaaccccga agtgtcgtcg gtgcgcgatt cggaccgcat cctgggcatc | 720 |
| ctggcctcca agaccaagcg cgccagcgaa ggcggcgacc cgatcaagga cacctgctg | 780 |
| atcaccgct acaaccccaa gcgtgtgcat ggcggcgaaa tgctgtcgct gaccgacatc | 840 |
| caggaaatcc tgcgcatcaa gctgatcggc gtggtgccgg agtctgaagc cgtgctgcac | 900 |
| gcctcgaacc agggcacgcc cgccatccac ctggaaggca cgacgtggc cgacgcctat | 960 |
| ggcgacgtgg tggaccgctt cctcggcaag gacaagccga tgcgtttcac cgactaccag | 1020 |
| aagccgggtc tgctctcccg catcttcggc aacaagtaac tgccggcct ggttcaacca | 1080 |
| gtcggcagcc gactagtgga tcc | 1103 |

<210> SEQ ID NO 19
<211> LENGTH: 1983
<212> TYPE: DNA
<213> ORGANISM: Artificial Sequence
<220> FEATURE:
<223> OTHER INFORMATION: Artificial DNA

<400> SEQUENCE: 19

| | |
|---|---|
| aagggccaat tgtacgccgc ccctgacca ggaacgccgg ccagtcccg gcgttttttt | 60 |
| attctatagc gcaattaacc gccgtcatat tgcgtcacca tgattgccgg atggccgcgg | 120 |
| cgatcccttg ctggaggccg gttccaagaa gatttaaaga tgtcacggaa ttgtcataca | 180 |
| gggagcatag agttcgtctt gtcaaaaatt tgtcattccc aaccaatgtt ctctggagga | 240 |
| catatgtccc agaagaaatc gccacgcttc gagctgcgca gtggcaacgt agacgccctc | 300 |
| cttctcgccc tccagaccgc cgacatggct gcgctgcggg atgacctcct cgcccgcttt | 360 |
| gaagccaccc ccgacttctt ttccaatgac gtgattgcgc tggacctgcg cgcgctggaa | 420 |

| | |
|---|---|
| gatgacagcg aagtcgcgct tggcaccgtg atcgagacgc tggccacgct cagggcccgc | 480 |
| gccatcggcg tggtggcccg ccccggccag cgcgagtggg ccgagcgctt cggcctgccg | 540 |
| ctgctggaca gccaggcccg ccgcggcagt ggcgccgatc gcgccaccga ccgtgccgcc | 600 |
| gaggccaggg ccgcagccgc ggcggaacag gccgcagccg accaggccgc gcgcgaggaa | 660 |
| tccatccgcg ccgccgcgca ggccaccacc gacgccgccg tggccgctgc catccgccag | 720 |
| acccagacca tgctgatcga caagccgctt cgctcgggcc agcaggtcta cgcgcagggc | 780 |
| gacgtggtca tcctggacgt ggtcagctac ggcgccgagg tgatcgccga aggcaacatc | 840 |
| catatctatg ccccgctgcg cggccgtgcg ctggcgggcg tcaagggcaa caccggcgcg | 900 |
| cgcattttca gcacgtgcat ggagcctgaa ctgatttcca tcgccggcat ctaccggacc | 960 |
| gcggagcaga cgcttccggc cgacgtgctc ggcaagaccg cccaggtgcg cctggccgat | 1020 |
| gaaaaactga tcctggaagc gctgcggctc aagtaaccgc ggcagccccc gggaccgaat | 1080 |
| tgcagagagc gcaagcttca acttattact ggaccaaaga gccatggcaa aaatcatcgt | 1140 |
| tgtgacctcc ggcaagggag gcgtcggcaa gaccaccacc agcgccagct tgccgccgg | 1200 |
| cctggccctg cgcggccaca agactgccgt gatcgacttc gacgtcggcc tgcgcaacct | 1260 |
| tgacctgatc atgggttgcg agcgccgcgt ggtgtacgac ctgatcaacg tggtgcaggg | 1320 |
| cgaagccaac ctgcgccagg cgctgatcaa ggacaagaag tgcgagaacc tgttcatcct | 1380 |
| gccggcctcg cagacgcgcg acaaggacgc gctcacgcgc gaaggcgtcg agaaggtcat | 1440 |
| caacggcctg atcgagatgg atttcgaatt catcatctgc gactcgccgg ccggcatcga | 1500 |
| gtcgggcgcg ctgatggcga tgtacttcgc cgacgaggcg ctgatcgtga ccaacccgga | 1560 |
| agtgtcgtcg gtgcgcgatt cggaccgcat cctgggcatc ctggcctcca agaccaagcg | 1620 |
| cgccagcgaa ggcggcgacc cgatcaagga acacctgctg atcacccgct acaacccccaa | 1680 |
| gcgtgtgcat ggcggcgaaa tgctgtcgct gaccgacatc caggaaatcc tgcgcatcaa | 1740 |
| gctgatcggc gtggtgccgg agtctgaagc cgtgctgcac gcctcgaacc agggcacgcc | 1800 |
| cgccatccac ctggaaggca gcgacgtggc cgacgcctat ggcgacgtgg tggaccgctt | 1860 |
| cctcggcaag gacaagccga tgcgtttcac cgactaccag aagcccgggtc tgctctcccg | 1920 |
| catcttcggc aacaagtaac ctgccggcct ggttcaacca gtcggcagcc gactagtgga | 1980 |
| tcc | 1983 |

<210> SEQ ID NO 20
<211> LENGTH: 2259
<212> TYPE: DNA
<213> ORGANISM: Artificial Sequence
<220> FEATURE:
<223> OTHER INFORMATION: Artificial DNA

<400> SEQUENCE: 20

| | |
|---|---|
| aagggccaat tgtacgccgc ccctgacca ggaacgccgg ccagtcccg gcgttttttt | 60 |
| attctatagc gcaattaacc gccgtcatat tgcgtcacca tgattgccgg atggccgcgg | 120 |
| cgatcccttg ctggaggccg gttccaagaa gatttaaaga tgtcacggaa ttgtcataca | 180 |
| gggagcatag agttcgtctt gtcaaaaatt tgtcattccc aaccaatgtt ctctggagga | 240 |
| catatgtccc agaagaaatc gccacgcttc gagctgcgca gtggcaacgt agacgccctc | 300 |
| cttctcgccc tccagaccgc cgacatggct gcgctgcggg atgacctcct cgcccgcttt | 360 |
| gaagccaccc ccgacttctt ttccaatgac gtgattgcgc tggacctgcg cgcgctggaa | 420 |

```
gatgacagcg aagtcgcgct tggcaccgtg atcgagacgc tggccacgct cagggcccgc    480
gccatcggcg tggtggcccg ccccggccag cgcgagtggg ccgagcgctt cggcctgccg    540
ctgctggaca gccaggcccg ccgcggcagt ggcgccgatc gcgccaccga ccgtgccgcc    600
gaggccaggg ccgcagccgc ggcggaacag gccgcagccg accaggccgc gcgcgaggaa    660
tccatccgcg ccgccgcgca ggccaccacc gacgccgccg tggccgctgc catccgccag    720
acccagacca tgctgatcga caagccgctt cgctcgggcc agcaggtcta cgcgcagggc    780
gacgtggtca tcctggacgt ggtcagctac ggcgccgagg tgatcgccga aggcaacatc    840
catatctatg ccccgctgcg cggccgtgcg ctggcgggcg tcaagggcaa caccggcgcg    900
cgcattttca gcacgtgcat ggagcctgaa ctgatttcca tcgccggcat ctaccggacc    960
gcggagcaga cgcttccggc cgacgtgctc ggcaagaccg cccaggtgcg cctggccgat   1020
gaaaaactga tcctggaagc gctgcggctc aagtaaccgc ggcagccccc gggaccgaat   1080
tgcagagagc gcaagcttca acttattact ggaccaaaga gccatggcaa aaatcatcgt   1140
tgtgacctcc ggcaagggag gcgtcggcaa gaccaccacc agcgccagct ttgccgccgg   1200
cctggccctg cgcggccaca agactgccgt gatcgacttc gacgtcggcc tgcgcaacct   1260
tgacctgatc atgggttgcg agcgccgcgt ggtgtacgac ctgatcaacg tggtgcaggg   1320
cgaagccaac ctgcgccagg cgctgatcaa ggacaagaag tgcgagaacc tgttcatcct   1380
gccggcctcg cagacgcgcg acaaggacgc gctcacgcgc gaaggcgtcg agaaggtcat   1440
caacggcctg atcgagatgg atttcgaatt catcatctgc gactcgccgg ccggcatcga   1500
gtcgggcgcg ctgatggcga tgtacttcgc cgacgaggcg ctgatcgtga ccaacccgga   1560
agtgtcgtcg gtgcgcgatt cggaccgcat cctgggcatc ctggcctcca agaccaagcg   1620
cgccagcgaa ggcggcgacc cgatcaagga cacctgctg atcacccgct acaaccccaa    1680
gcgtgtgcat ggcggcgaaa tgctgtcgct gaccgacatc caggaaatcc tgcgcatcaa   1740
gctgatcggc gtggtgccgg agtctgaagc cgtgctgcac gcctcgaacc agggcacgcc   1800
cgccatccac ctggaaggca gcgacgtggc cgacgcctat ggcgacgtgg tggaccgctt   1860
cctcggcaag gacaagccga tgcgtttcac cgactaccag aagccgggtc tgctctcccg   1920
catcttcggc aacaagtaac ggtcaaggag ggctcacccc atgtcgatcc tttccttcct   1980
gctgggagag aagaagaagt ccgcgtcggt cgccaaggag cggctgcaga tcatcctggc   2040
gcacgagcgc accggccatt ccgcgcccgc cgactacctg cccgcgctgc agcgcgagct   2100
ggtggcggtg atttccaagt acgtcaagat cggcgaccag gacctgcgcg tcagcctgga   2160
gcgccaggac aacctcgagg tgctcgaggt caagatcgag atcccgcaga actgacctgc   2220
cggcctggtt caaccagtcg gcagccgact agtggatcc                          2259
```